(12) United States Patent
Laayoun et al.

(10) Patent No.: US 8,663,923 B2
(45) Date of Patent: Mar. 4, 2014

(54) DETECTION PROBE

(75) Inventors: Ali Laayoun, Colombe (FR); Eloy Bernal Mendez, Saint Quentin Fallavier (FR)

(73) Assignee: bioMerieux, Marcy l'Etoile ( * ) Notice: Subject to any disclaimer, the term of this patent is extended or adjusted under 35 U.S.C. 154(b) by 0 days.

(21) Appl. No.: 12/996,457

(22) PCT Filed: Jul. 3, 2009

(86) PCT No.: PCT/FR2009/051315
§ 371 (c)(1),
(2), (4) Date: Dec. 6, 2010

(87) PCT Pub. No.: WO2010/001074
PCT Pub. Date: Jan. 7, 2010

(65) Prior Publication Data
US 2011/0091898 A1    Apr. 21, 2011

(30) Foreign Application Priority Data
Jul. 4, 2008    (FR) ...................... 08 54549

(51) Int. Cl.
*C12Q 1/68*    (2006.01)
*C07H 21/04*    (2006.01)

(52) U.S. Cl.
USPC ........................................ 435/6.12; 536/24.3

(58) Field of Classification Search
USPC ........................................ 435/6.12; 536/24.3
See application file for complete search history.

(56) References Cited

U.S. PATENT DOCUMENTS

| | | | |
|---|---|---|---|
| 5,866,336 A | 2/1999 | Nazarenko et al. | |
| 6,037,130 A | 3/2000 | Tyagi et al. | |
| 6,117,635 A | 9/2000 | Nazarenko et al. | |
| 7,019,129 B1 | 3/2006 | Cook et al. | |
| 8,067,165 B2 | 11/2011 | Livak et al. | |
| 2003/0059786 A1* | 3/2003 | Ward et al. ..................... | 435/6 |
| 2003/0134307 A1 | 7/2003 | Beckman et al. | |
| 2005/0059049 A1 | 3/2005 | Moen et al. | |

(Continued)

FOREIGN PATENT DOCUMENTS

EP    0 569 272 A1    11/1993
WO    WO 88/04301 A1    6/1988

(Continued)

OTHER PUBLICATIONS

Tsourkas et al. Nucleic Acids Research. 30(19): 4208-4215. 2002.*

(Continued)

*Primary Examiner* — Robert T Crow
*Assistant Examiner* — Joseph G Dauner
(74) *Attorney, Agent, or Firm* — Oliff PLC

(57) ABSTRACT

A nucleotide probe permitting the detection of nucleic acids and constituted of a labeled nucleotide strand having three fragments: a first fragment having a first closing sequence, a second fragment, all or part of which has a recognition sequence for the molecular recognition of the target nucleic acid and a third fragment having a second closing sequence, and at least two markers, one of the ends of the strand of the detection probe being free of any marker, in which, when the two closing sequences are hybridized together, the detection probe has a completely circular shape, the closing sequences thus maintaining the probe in a conformation that cannot be detected in the absence of the target nucleic acid.

8 Claims, 10 Drawing Sheets

Nucleotide 1

Nucleotide 2

Nucleotide 3

(56) References Cited

U.S. PATENT DOCUMENTS

Figure 1:
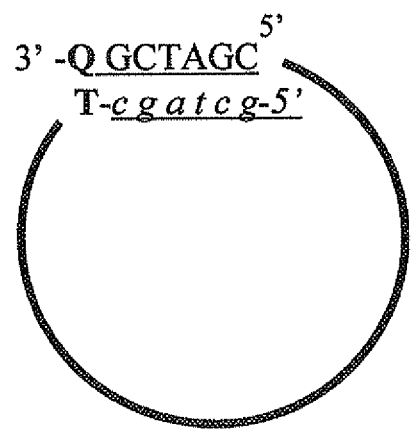

| | | | |
|---|---|---|---|
| 2006/0183120 A1* | 8/2006 | Teh et al. ..................... | 435/6 |
| 2006/0246438 A1* | 11/2006 | McCall et al. ................ | 435/6 |
| 2007/0020656 A1 | 1/2007 | Sorge | |
| 2009/0104614 A1 | 4/2009 | Tsourkas et al. | |
| 2009/0280477 A1 | 11/2009 | Coull et al. | |

FOREIGN PATENT DOCUMENTS

| | | |
|---|---|---|
| WO | WO 90/15813 A1 | 12/1990 |
| WO | WO 95/13399 | 5/1995 |
| WO | WO 96/19240 A1 | 6/1996 |
| WO | WO 00/32810 | 6/2000 |
| WO | WO 2007/114986 A2 | 10/2007 |

OTHER PUBLICATIONS

Leone. Nucleic Acids Research. 1998. 26(9): 2150-2155.*
Nilsson. Nucleic Acids Research. 2002. 30(14): e66.*
Belanger et al., "Rapid Detection of Shiga Toxin-Producing Bacteria in Feces by Multiplex PCR with Molecular Beacons on the Smart Cycler," Journal of Clinical Microbiology, Apr. 2002, vol. 40, No. 4, pp. 1436-1440.
Ishchenko et al., "Uncoupling of the Base Excision and Nucleotide Incision Repair Pathways Reveals Their Respective Biological Roles," PNAS, vol. 103, No. 8; pp. 2564-2569, Feb. 21, 2006.
Jul. 1, 2011 Office Action issued in U.S. Appl. No. 12/310,556.
Tyagi, Sanjay et al., "Molecular Beacons: Probes that Fluoresce upon Hybridization", Nature Biotechnology, Mar. 1996, pp. 303-308, vol. 14, Department of Molecular Genetics, Public Health Research Institute, New York, NY.
Morvan et al., "Solid Phase Synthesis of α-anomeric oligodeoxyribonucleotides," Nucleic Acids Research 16 (3); pp. 833-847; 1988.
Oct. 7, 2010 Office Action issued in U.S. Appl. No. 12/310,556.
Jun. 16, 2008 International Search Report issued in PCT/FR2007/052007 (with Translation).
Yl et al., "Molecular Zipper: A Fluorescent Probe for Real-Time Isothermal DNA Amplification," Nucleic Acids Research, Oxford University Press, vol. 34, No. 11, 2006, pp. 1-5.
Zhang et al., "Detection of Target Nucleic Acids and Proteins by Amplification of Circularizable Probes, Expert Review of Molecular Diagnostics, Future Drugs," London, GB, vol. 3, No. 2, 2003, pp. 237-248.
Zhang et al., "Amplification of Circularizable Probes for the Detection of Target Nucleic Acids and Proteins," Clinica Chimica Acta, Elsevier, BV, Amsterdam, vol. 363, No. 1-2, 2006, pp. 61-70.
Weusten et al., "Principles of Quantitation of Viral Loads Using Nucleic Acid Sequence-Based Amplification in Combination With Homogeneous Detection Using Molecular Beacons," Nucleic Acids Research, 2002, Oxford University Press, vol. 30, No. 6, pp. 1-7.
Koga et al., "Alternating α,β-Oligothymidylates with Alternating (3'→3')- and (5'→5')-Internucleotidic Phosphodiester Linkages as Models for Antisense Oligodeoxyribonueleotides," The Journal of Organic Chemistry, vol. 56, No. 12, Jun. 7, 1991, pp. 3757-3759.

Tsourkas et al., "Structure-Function Relationships of Shared-Stem and Conventional Molecular Beacons," Nucleic Acids Research, Oxford University Press, Oct. 2002, vol. 30, No. 19, pp. 4208-4215.
Browne, "Sequence-Specific, Self-Reporting Hairpin Inversion Probes," J. Am. Chem. Soc. 2005, vol. 127, pp. 1989-1994.
Crey-Desbiolles et al., "Molecular Beacons With a Homo-DNA Stem: Improving Target Selectivity," Nucleic Acids Research, 2005, vol. 33, No. 8, pp. 1-7.
Co-pending U.S. Appl. No. 12/225,693, filed Sep. 26, 2008, Eloy Bernal Mendez et al.
Co-pending U.S. Appl. No. 12/310,556, filed Feb. 27, 2009, Eloy Bernal Mendez et al.
Co-pending U.S. Appl. No. 12/926,962, filed Dec. 20, 2010, Eloy Bernal Mendez et al.
Jan. 7, 2010 Office Action issued in U.S. Appl. No. 12/225,693.
Aug. 19, 2010 Office Action issued in U.S. Appl. No. 12/225,693.
Mar. 5, 2010 Office Action issued in U.S. Appl. No. 12/225,693.
Shchepinov et al., "Oligonucleotide Dendrimers: Synthesis and Use as Polylabelled DNA Probes," Nucelic Acids Research, vol. 25, No. 22, pp. 4447-4454, 1997.
Afonina et al., "Minor Groove Binder-Conjugated DNA Probes for Quantitative DNA Detection by Hybridization-Triggered Fluorescence," Biotechniques, vol. 32, No. 4, pp. 940-949, 2002.
Feb. 14, 2008 International Search Report issued in PCT/FR2007/051159.
Striebel et al., "Enhancing Sensitivity of Human Herpes Virus Diagnosis with DNA Microarrays Using Dendrimers," Experimental and Molecular Pathology, vol. 77, 2004, pp. 89-97.
Mar. 31, 2011 Office Action issued in U.S. Appl. No. 12/310,556.
Hirose et al., "Formation and Stability of Alternate-Stranded Triplex Formed With Alpha, Beta-Chimeric OligoDNA," Nucleic Acids Research Supplement 2, pp. 263-264, 2002 Oxford University Press.
Jan. 10, 2012 Office Action issued in U.S. Appl. No. 12/926,962.
Jan. 24, 2012 Notice of Allowance issued in U.S. Appl. No. 12/310,556.
Aramino et al., Solution Structure of a DNA Duplex Containing an α-Anomeric Adenosine: Insights into Substrate Recognition by Endonuclease IV. J. of Molecular Biology 338:77-91 (2004).
Vichier-Geurre et al., New Insights into the Resistance of α-Oligonucleotides to Nucleases. Antisense Research and Development 4: 9-18 (1994).
Cazenave et al., Rate of degradation of [α]-and [β]-oligodeoxynucleotides in *Xenopus* oocytes. Implications for anti-messenger strategies. Nucleic Acids Res. 15: 10507-10521 (1987).
Jun. 28, 2012 Office Action issued in U.S. Appl. No. 12/926,962.
Dec. 28, 2012 Office Action issued in U.S. Appl. No. 12/926,962.
Marras; "Selection of Fluorophore and Quencher Pairs for Fluorescent Nucleic Acid Hybridization Probes;" Methods Mol. Biol.; 2006; vol. 335; pp. 3-16.
Marras et al.; "Real-time assays with molecular beacons and other fluorescent nucleic acid hybridization probes;" Clin. Chim. Acta.; Jan. 2006; vol. 363; pp. 48-60.
Oct. 7, 2013 Office Action issued in U.S. Appl. No. 12/926,962.

* cited by examiner

SEQUENCE LISTING

```
<160> NUMBER OF SEQ ID NOS: 50

<210> SEQ ID NO 1
<211> LENGTH: 37
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(9)
<223> OTHER INFORMATION: nucleic acid with an anomeric alpha
      configuration

<400> SEQUENCE: 1
gaccgtctgt ggagaagacg tccaaaaact ggcagac                            37

<210> SEQ ID NO 2
<211> LENGTH: 44
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(10)
<223> OTHER INFORMATION: nucleic acid with an anomeric alpha
      configuration

<400> SEQUENCE: 2
accctatctc tccatcaatg aggaagctgc agaatgggat agag                    44

<210> SEQ ID NO 3
<211> LENGTH: 26
<212> TYPE: DNA
<213> ORGANISM: Artificial Sequence
<220> FEATURE:
<223> OTHER INFORMATION: Synthetic Construct--Target

<400> SEQUENCE: 3
tttagttttt ggacgtcttc tcctttt                                      26

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct--Target

<400> SEQUENCE: 4
```
tttactctat cccattctgc agcttcctca ttgatttt                              38

<210> SEQ ID NO 5
<211> LENGTH: 36
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(27)
<223> OTHER INFORMATION: natural nucleotides carrying (5'-3')
      phosphodiester linkages
<220> FEATURE:
<221> NAME/KEY: misc_feature
<222> LOCATION: (28)..(36)
<223> OTHER INFORMATION: inverted nucleotides

<400> SEQUENCE: 5
ggagaagacg tccaaaaact ggcagatcct cttctg                               36

<210> SEQ ID NO 6
<211> LENGTH: 45
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(34)
<223> OTHER INFORMATION: natural nucleotides carrying (5'-3')
      phosphodiester linkages
<220> FEATURE:
<221> NAME/KEY: misc_feature
<222> LOCATION: (35)..(45)
<223> OTHER INFORMATION: inverted nucleotides

<400> SEQUENCE: 6
ccatcaatga ggaagctgca gaatgggata gagtggtagt tactc                     45

<210> SEQ ID NO 7
<211> LENGTH: 47
<212> TYPE: DNA
<213> ORGANISM: Artificial Sequence
<220> FEATURE:
<223> OTHER INFORMATION: Synthetic Construct--Promoter and primer

<400> SEQUENCE: 7
aattctaata cgactcacta tagggagct ctgctttagc acttcca                    47

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct--Primer

<400> SEQUENCE: 8
gagaaatgca gatggtctca gcta                                            24

<210> SEQ ID NO 9
<211> LENGTH: 54
<212> TYPE: DNA
<213> ORGANISM: Artificial Sequence
<220> FEATURE:
<223> OTHER INFORMATION: Synthetic Construct--Primer and promoter

<400> SEQUENCE: 9
aattctaata cgactcacta tagggtgcta tgtcacttcc ccttggttct ctca           54

<210> SEQ ID NO 10
<211> LENGTH: 29
<212> TYPE: DNA
<213> ORGANISM: Artificial Sequence
<220> FEATURE:
<223> OTHER INFORMATION: Synthetic Construct--Primer

<400> SEQUENCE: 10
agtgggggga catcaagcag ccatgcaaa                              29

<210> SEQ ID NO 11
<211> LENGTH: 40
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(9)
<223> OTHER INFORMATION: nucleic acid with an anomeric alpha
      configuration

<400> SEQUENCE: 11
accctatcct atcaatgagg aagctgcaga atgggatagg                  40

<210> SEQ ID NO 12
<211> LENGTH: 43
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(33)
<223> OTHER INFORMATION: natural nucleotides carrying (5'-3')
      phosphodiester linkages
<220> FEATURE:
<221> NAME/KEY: misc_feature
<222> LOCATION: (34)..(43)
<223> OTHER INFORMATION: inverted nucleotides

<400> SEQUENCE: 12
ccatcaatga ggaagctgca gaatgggata ggtggtagtt act              43

<210> SEQ ID NO 13
<211> LENGTH: 32
<212> TYPE: DNA
<213> ORGANISM: Artificial Sequence
<220> FEATURE:
<223> OTHER INFORMATION: Synthetic Construct--Probe

<400> SEQUENCE: 13
cgatcgggag aagacgtcca aaaactcgat cg                          32

<210> SEQ ID NO 14
<211> LENGTH: 37
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(9)
<223> OTHER INFORMATION: nucleic acid with an anomeric alpha
      configuration

<400> SEQUENCE: 14
gagcgtagct ggagaagacg tccaaaaact cgcatcg                     37

-continued

```
<210> SEQ ID NO 15
<211> LENGTH: 35
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(8)
<223> OTHER INFORMATION: nucleic acid with an anomeric alpha
      configuration

<400> SEQUENCE: 15
gagctagctg gagaagacgt ccaaaaactc gatcg                              35

<210> SEQ ID NO 16
<211> LENGTH: 35
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(8)
<223> OTHER INFORMATION: inverted nucleotides
<220> FEATURE:
<221> NAME/KEY: misc_feature
<222> LOCATION: (9)..(35)
<223> OTHER INFORMATION: natural nucleotides carrying (5'-3')
      phosphodiester linkages

<400> SEQUENCE: 16
gagctagctg gagaagacgt ccaaaaactc gatcg                              35

<210> SEQ ID NO 17
<211> LENGTH: 35
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(7)
<223> OTHER INFORMATION: inverted nucleotides
<220> FEATURE:
<221> NAME/KEY: misc_feature
<222> LOCATION: (8)..(35)
<223> OTHER INFORMATION: natural nucleotides carrying (5'-3')
      phosphodiester linkages

<400> SEQUENCE: 17
gctagcctgg agaagacgtc caaaaactcg atcgg                              35

<210> SEQ ID NO 18
<211> LENGTH: 26
<212> TYPE: DNA
<213> ORGANISM: Artificial Sequence
<220> FEATURE:
<223> OTHER INFORMATION: Synthetic Construct--Target

<400> SEQUENCE: 18
tttagttttt ggaggtcttc tccttt                                        26

<210> SEQ ID NO 19
<211> LENGTH: 26
<212> TYPE: DNA
<213> ORGANISM: Artificial Sequence
<220> FEATURE:
<223> OTHER INFORMATION: Synthetic Construct--Target

<400> SEQUENCE: 19
```
tttagttttt ggaagtcttc tcctttt          26

<210> SEQ ID NO 20
<211> LENGTH: 26
<212> TYPE: DNA
<213> ORGANISM: Artificial Sequence
<220> FEATURE:
<223> OTHER INFORMATION: Synthetic Construct--Target

<400> SEQUENCE: 20
tttagttttt ggatgtcttc tcctttt          26

<210> SEQ ID NO 21
<211> LENGTH: 36
<212> TYPE: DNA
<213> ORGANISM: Artificial Sequence
<220> FEATURE:
<223> OTHER INFORMATION: Synthetic Construct--Probe

<400> SEQUENCE: 21
ctatcccatc aatgaggaag ctgcagaatg ggatag          36

<210> SEQ ID NO 22
<211> LENGTH: 39
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(10)
<223> OTHER INFORMATION: nucleic acid with an anomeric alpha
      configuration

<400> SEQUENCE: 22
ttaccctatc ttcaatgagg aagctgcaga atgggatag          39

<210> SEQ ID NO 23
<211> LENGTH: 44
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(33)
<223> OTHER INFORMATION: natural nucleotides carrying (5'-3')
      phosphodiester linkages
<220> FEATURE:
<221> NAME/KEY: misc_feature
<222> LOCATION: (34)..(44)
<223> OTHER INFORMATION: inverted nucleotides

<400> SEQUENCE: 23
ccatcaatga ggaagctgca gaatgggata ggtggtagtt actc          44

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct--Target

<400> SEQUENCE: 24
tttcattctg cagcttcctc attt          24

<210> SEQ ID NO 25
<211> LENGTH: 24

```
<212> TYPE: DNA
<213> ORGANISM: Artificial Sequence
<220> FEATURE:
<223> OTHER INFORMATION: Synthetic Construct--Target

<400> SEQUENCE: 25
tttcattctg caggttcctc attt                                           24

<210> SEQ ID NO 26
<211> LENGTH: 24
<212> TYPE: DNA
<213> ORGANISM: Artificial Sequence
<220> FEATURE:
<223> OTHER INFORMATION: Synthetic Construct--Target

<400> SEQUENCE: 26
tttcattctg cagattcctc attt                                           24

<210> SEQ ID NO 27
<211> LENGTH: 24
<212> TYPE: DNA
<213> ORGANISM: Artificial Sequence
<220> FEATURE:
<223> OTHER INFORMATION: Synthetic Construct--Target

<400> SEQUENCE: 27
tttcattctg cagtttcctc attt                                           24

<210> SEQ ID NO 28
<211> LENGTH: 33
<212> TYPE: DNA
<213> ORGANISM: Artificial Sequence
<220> FEATURE:
<223> OTHER INFORMATION: Synthetic Construct--Target

<400> SEQUENCE: 28
tttagttttt ggacgtcttc tccttttcca att                                 33

<210> SEQ ID NO 29
<211> LENGTH: 33
<212> TYPE: DNA
<213> ORGANISM: Artificial Sequence
<220> FEATURE:
<223> OTHER INFORMATION: Synthetic Construct--Target

<400> SEQUENCE: 29
tttagttttt ggacgtcttc tcccgatcga att                                 33

<210> SEQ ID NO 30
<211> LENGTH: 33
<212> TYPE: DNA
<213> ORGANISM: Artificial Sequence
<220> FEATURE:
<223> OTHER INFORMATION: Synthetic Construct--Target

<400> SEQUENCE: 30
tttagttttt ggacgtcttc tccacagacg gtc                                 33

<210> SEQ ID NO 31
<211> LENGTH: 33
<212> TYPE: DNA
<213> ORGANISM: Artificial Sequence
<220> FEATURE:
<223> OTHER INFORMATION: Synthetic Construct--Target

<400> SEQUENCE: 31
tttagttttt ggacgtcttc tccacagaca att                                 33
```

<210> SEQ ID NO 32
<211> LENGTH: 33
<212> TYPE: DNA
<213> ORGANISM: Artificial Sequence
<220> FEATURE:
<223> OTHER INFORMATION: Synthetic Construct--Target

<400> SEQUENCE: 32
tttagttttt ggacgtcttc tccctttcca att                                    33

<210> SEQ ID NO 33
<211> LENGTH: 33
<212> TYPE: DNA
<213> ORGANISM: Artificial Sequence
<220> FEATURE:
<223> OTHER INFORMATION: Synthetic Construct--Target

<400> SEQUENCE: 33
tttagttttt ggacgtcttc tccatttcca att                                    33

<210> SEQ ID NO 34
<211> LENGTH: 33
<212> TYPE: DNA
<213> ORGANISM: Artificial Sequence
<220> FEATURE:
<223> OTHER INFORMATION: Synthetic Construct--Target

<400> SEQUENCE: 34
tttagttttt ggacgtcttc tcccgttcca att                                    33

<210> SEQ ID NO 35
<211> LENGTH: 33
<212> TYPE: DNA
<213> ORGANISM: Artificial Sequence
<220> FEATURE:
<223> OTHER INFORMATION: Synthetic Construct--Target

<400> SEQUENCE: 35
tttagttttt ggacgtcttc tccacttcca att                                    33

<210> SEQ ID NO 36
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 36
tttcattctg cagcttcctc attgatggtc tcttttaac                              39

<210> SEQ ID NO 37
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 37
tttcattctg cagcttcctc attgatggga tagtttaac                              39

<210> SEQ ID NO 38
<211> LENGTH: 39
<212> TYPE: DNA
<213> ORGANISM: Artificial Sequence

```
<220> FEATURE:
<223> OTHER INFORMATION: Synthetic Construct--Target

<400> SEQUENCE: 38
tttcattctg cagcttcctc attgatggag agatagggt                               39

<210> SEQ ID NO 39
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 39
tttcattctg cagcttcctc attgatggag agatttaac                               39

<210> SEQ ID NO 40
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 40
tttcattctg cagcttcctc attgatgggc tcttttaac                               39

<210> SEQ ID NO 41
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 41
tttcattctg cagcttcctc attgatggac tcttttaac                               39

<210> SEQ ID NO 42
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 42
tttcattctg cagcttcctc attgatggga tcttttaac                               39

<210> SEQ ID NO 43
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 43
tttcattctg cagcttcctc attgatggag tcttttaac                               39

<210> SEQ ID NO 44
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 44
ttgcagctct tctgccagtt tttggacgtc ttctcctttt                              39
```

```
<210> SEQ ID NO 45
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 45
ttgccgatcg tctgccagtt tttggacgtc ttctcctttt                              39

<210> SEQ ID NO 46
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 46
cagaagagga tctgccagtt tttggacgtc ttctcctttt                              39

<210> SEQ ID NO 47
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 47
ttgcagagga tctgccagtt tttggacgtc ttctcctttt                              39

<210> SEQ ID NO 48
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 48
ttgcagctcg tctgccagtt tttggacgtc ttctcctttt                              39

<210> SEQ ID NO 49
<211> LENGTH: 39
<212> TYPE: DNA
<213> ORGANISM: Artificial Sequence
<220> FEATURE:
<223> OTHER INFORMATION: Synthetic Construct--Target

<400> SEQUENCE: 49
ttgcagctca tctgccagtt tttggacgtc ttctcctttt                              39

<210> SEQ ID NO 50
<211> LENGTH: 44
<212> TYPE: DNA
<213> ORGANISM: Artificial Sequence
<220> FEATURE:
<223> OTHER INFORMATION: Synthetic Construct--Probe
<220> FEATURE:
<221> NAME/KEY: misc_feature
<222> LOCATION: (1)..(10)
<223> OTHER INFORMATION: inverted nucleotides
<220> FEATURE:
<221> NAME/KEY: misc_feature
<222> LOCATION: (11)..(44)
<223> OTHER INFORMATION: natural nucleotides carrying (5'-3')
      phosphodiester linkages

<400> SEQUENCE: 50
accctatctc tccatcaatg aggaagctgc agaatgggat agag                         44
```

DETECTION PROBE

The present invention relates to the detection of nucleic acids by novel nucleotide probes. The invention finds application in the field of diagnosis.

Nowadays, finding target nucleotide sequences represents a major objective in numerous laboratories and especially in the medical or food-processing field. In these fields, finding target sequences has the aim for example of detecting pathogenic organisms, finding bacterial contamination in a food-processing chain or the diagnosis of mutations that are responsible for genetic diseases or cancers. The main difficulties in these methods concern the specificity, sensitivity, speed and reproducibility of the test used. It is absolutely essential to be able to give a definite result, particularly in the area of diagnosis.

Various types of methods are described in the literature. They are generally based on the properties of pairing complementary strands of nucleic acids, commonly called "hybridization of nucleic acids" or simply "hybridization".

Generally, after determining the specific sequence of an organism or of a disease that must be analyzed, it is necessary to extract the nucleic acids from a sample, and optionally amplify and detect the sequence of interest. A great many methods of amplification have been developed, such as PCR, LCR, NASBA, TMA, SDA. There are also many techniques for detection. One of these employs special probes, described by Tyagi and Kramer (Nature Biotech, 1996, 14:303-308), commonly called "molecular beacons". These probes have a hairpin structure comprising a single-stranded "loop" part and a double-stranded "stem" part. The "loop" part contains a complementary sequence to the target nucleotide sequence and the "stem" part is formed by two sequences that are complementary to one another. The free end of one of the complementary sequences of the "stem" part is labeled with a fluorophore whereas the other free end of the other strand of the "stem" part is coupled to a fluorescence quencher. In the absence of a complementary target sequence, the detection probe is hairpin-shaped and the probe does not produce fluorescence, the energy of the fluorophore being transferred directly to the fluorescence quencher. When this probe hybridizes to a target sequence, it loses its configuration, the 5' and 3' ends move farther apart and the fluorescence quencher and the fluorophore are separated from one another. The fluorescence emitted then reflects the hybridization of the probe on the target, which is detected during its amplification and optionally quantified. This is then called real-time homogeneous-phase detection. However, these molecular beacon probes can display undesirable premature opening of the "stem" part in the presence of certain contaminants. It has in fact been observed that molecular beacon probes interact, by unknown mechanisms, with the enzymes present in the reaction mixture, such as that used in an amplification of the NASBA type for example. These interactions occur even in the absence of any biological target and are responsible for an increase in the nonspecific fluorescence signal.

Molecular beacon probes have important synthesis constraints necessitating a quite particular design for the sequences of the stem. In fact, they can hybridize nonspecifically to the target to be detected, notably when the latter is rich in GC bases, inducing false positives or considerable background noise, affecting the sensitivity of detection. Moreover, it is necessary to introduce two complementary sequences to form the stem; the complete sequence of the hairpin probe then comprises at least 30 nucleotides, whereas only 20 nucleotides are generally necessary for molecular recognition. Accordingly, the yield in synthesis of these hairpin probes is fairly limited. Another drawback of these probes is the difficulty of designing the hairpin structure because of the "stem-loop" structure which facilitates folding of the loop back on itself and internal "loop-loop" interactions. Thus, several designs and syntheses are then often necessary before the sequence possessing the required thermodynamic characteristics is found.

Various solutions have been proposed to try to overcome the problem of nonspecific hybridization of the stem. Thus, Crey-Desbiolles et al. (Nucleic Acids Res., May 2005; 33: e77) proposed replacing the natural nucleotides of the stem with modified nucleotides that hybridize to one another to form the stem but cannot hybridize to the natural nucleotides of the target. The main drawback of this approach is the need to introduce, at each end of the recognition sequence, at least four or five units of this modified nucleotide, but it is not commercially available, which makes the synthesis of the hairpin probe more complicated. Moreover, this approach does not solve the problem of the large number of nucleotides of the complete sequence nor the problem of the difficulty of designing the hairpin structure.

Another solution proposed by Browne (J. Am. Chem. Soc., 2005, 127, 1989-1994) consists of inserting inverted nucleotides into the two sequences of the stem. In this embodiment, the sequences of the stem cannot hybridize directly to the sequences of the target adjoining the sequence hybridized to the loop, because of their parallel orientation with the target. The drawback of this technique is that the sequences of the stem can interact with other more distant sequences of the target which could fold and become accessible for this interaction. Moreover, the problems of the large number of nucleotides of the complete sequence and of the instability of the hairpin structure are not solved by this approach.

Another solution proposed by Tsourkas et al. (Nucleic Acids Res., October 2002; 30: 4208-4215) consists of designing the hairpin probe in such a way that one of the sequences forming the stem also forms part of the recognition sequence. This solution makes it possible to shorten the complete sequence of the probe. However, a loss of specificity associated with this design has been observed. Moreover, for the same recognition sequence, this type of design has a shorter loop, which restricts its flexibility and reinforces the loop-loop interactions, making the thermodynamic characteristics of the probe less predictable.

There is therefore a real need for a new probe format permitting the drawbacks of the prior art to be overcome.

Accordingly, the invention relates to a novel probe for detecting a target nucleic acid, constituted of a labeled nucleotide strand comprising three fragments:
 a first fragment having a first closing sequence,
 a second fragment, all or part of which has a recognition sequence intended for molecular recognition of the target nucleic acid,
 a third fragment having a second closing sequence, and
 at least two markers, one of the ends of the strand of said detection probe being free of any marker,
in which, when the two closing sequences are hybridized together, the detection probe has a completely circular shape, said closing sequences thus maintaining said probe in a conformation that cannot be detected in the absence of said target nucleic acid. "Completely circular" means a conformation of the probe in which the two closing sequences are hybridized to one another to form a duplex, one of the ends of one of the closing sequences being connected to the opposite end of the other closing sequence via the recognition sequence, the whole forming a circle as in FIGS. 1 and 2. In contrast to a hairpin structure, this conformation makes it possible to maintain the loop sequence in a linear arrangement, stretched between the two ends of the stem, which prevents internal interactions in the sequence of the loop, and also facilitates its accessibility by the complementary target.

In an interesting embodiment of the invention, the detection probe is characterized in that a first marker is carried by a nucleotide of the first fragment and a second marker is carried by a nucleotide of the second or of the third fragment, the two nucleotides being adjacent when the two closing sequences are hybridized.

According to a preferred embodiment of the invention, the detection probe is characterized in that all or part of the two closing sequences are hybridized in parallel. Advantageously, one of the closing sequences is a sequence constituted of alpha-anomeric nucleotides.

According to another preferred embodiment of the invention, the detection probe is characterized in that all or part of the two closing sequences are hybridized in antiparallel. Advantageously, one of the two closing sequences is bound to the recognition sequence by a 5'-5' or 3'-3' inverted bond.

Advantageously, at least one marker is a fluorophore and at least one other marker is a fluorescence quencher. Thus, when the two closing sequences are hybridized together, the nucleotides bearing the markers are adjacent, so that all or a large part of the energy of the fluorophore after excitation is transferred to the fluorescence quencher. Preferably, the two markers are carried by nucleotides positioned opposite each other, these two nucleotides being joined together by hydrogen bonds, forming a base pairing, or 1 to 5 nucleotides apart.

Advantageously, all or part of the first or of the second closing sequence can hybridize to the target sequence. This conformation provides better control of the gap between the fluorophore and the fluorescence quencher; since one of the closing sequences is immobilized on the target, the two closing sequences cannot approach one another as much as if they were both in a flexible single-stranded conformation. This conformation also has the advantage of reducing the number of free nucleotides that can interact nonspecifically and of reducing the number of nucleotides of the complete sequence. Advantageously, the length of the probe is between 25 and 40 nucleotides.

According to the preceding embodiment, once hybridized to the target sequence, the probe has a closing sequence that participates in hybridization whereas the other closing sequence is incapable of hybridizing owing to its inverted orientation or the presence of alpha nucleotides. This conformation makes it possible to limit nonspecific hybridizations. Moreover, during design of the probe, addition of the modified (alpha or inverted) closing sequence to the rest of the probe does not affect the design of the recognition sequence. Thus, design is limited to defining the proper complementary sequence of the target in relation to the detection conditions, and afterwards adding to one of its ends a modified (alpha or inverted) closing sequence complementary to the other closing sequence capable of hybridizing to the target, without having to verify the possible interactions with the target or having to add a sequence to each end, as is the case for hairpin probes. This therefore facilitates design of the probe.

Also advantageously, the length of the closing sequences is between 6 and 30 nucleotides, preferably between 6 and 15 nucleotides.

In a particular embodiment, a nucleotide sequence is attached to the detection probe. Preferably, it is attached to the end of the natural closing sequence, i.e. to the sequence which is neither inverted nor constituted of alpha nucleotides. Thus, the detection probe according to the present invention can be adapted to the probe design called "tentacle probe" according to patent application WO-A-07/114,986.

The detection probe according to the present invention can be employed in any test where a nucleotide probe is used for detecting a target nucleic acid. Thus, another object of the present invention relates to a method for detecting a target sequence that may be present in a sample, comprising the following stages:

contacting the sample with a detection probe according to the present invention, detecting the formation of a hybrid between the detection probe and the target sequence, indicating the presence of said target sequence in said sample.

In a preferred embodiment of the invention, detection is carried out together with a reaction of amplification of the target sequence; this is then called real-time detection. In another preferred embodiment, detection is carried out after a reaction of amplification of the target sequence; this is then called "end-point" detection. The amplification reaction can be based on any method of amplification, linear or exponential, such as PCR, LCR, NASBA, TMA, SDA, RCA. Preferably, the method of amplification is a method of amplification producing single-stranded DNA or RNA nucleic acids, such as NASBA, TMA or asymmetric PCR.

Another object of the invention relates to a kit for detecting a target sequence comprising at least one detection probe according to the present invention. This kit can optionally contain the reagents and primer sequences necessary for carrying out an amplification reaction. For example, a kit according to the present invention, suitable for a NASBA amplification, can contain nucleotides and amplification enzymes such as reverse transcriptases, RNase H and T7 RNA polymerase.

The following definitions will provide better understanding of the invention.

The term "nucleic acid" or "nucleotide sequence" means a chain of at least two deoxyribonucleotides or ribonucleotides optionally comprising at least one modified nucleotide, for example at least one nucleotide having a modified nucleic acid base, such as inosine, methyl-5-deoxycytidine, dimethylamino-5-deoxyuridine, deoxyuridine, diamino-2,6-purine, bromo-5-deoxyuridine or any other modified base permitting hybridization. This polynucleotide can also be modified at the level of the internucleotide bond for example phosphorothioates, H-phosphonates, alkyl phosphonates, at the level of the backbone for example alpha-oligonucleotides (FR 2 607 507) or PNAs (M. Egholm et al., J. Am. Chem. Soc., 114, 1895-1897, 1992) or 2'-O-alkyl ribose and LNAs (BW, Sun et al., Biochemistry, 4160-4169, 43, 2004). The nucleic acid can be natural or synthetic, an oligonucleotide, a polynucleotide, a nucleic acid fragment, a ribosomal RNA, a messenger RNA, a transfer RNA, a nucleic acid obtained by an enzymatic amplification technique, such as:

PCR (Polymerase Chain Reaction), described in U.S. Pat. No. 4,683,195, U.S. Pat. No. 4,683,202 and U.S. Pat. No. 4,800,159, and its derivative RT-PCR (Reverse Transcription PCR), notably in a single-stage format, as described in patent EP-B-0,569,272, LCR (Ligase Chain Reaction), disclosed for example in patent application EP-A-0,201,184, RCR (Repair Chain Reaction), described in patent application WO-A-90/01069, 3SR (Self-Sustained Sequence Replication) with patent application WO-A-90/06995, NASBA (Nucleic Acid Sequence-Based Amplification) with patent application WO-A-91/02818, TMA (Transcription Mediated Amplification) with U.S. Pat. No. 5,399,491, and RCA (Rolling Circle Amplification) described in U.S. Pat. No. 6,576,448.

In the sense of the present invention, "target" or "target nucleic acid" means a nucleotide sequence in which at least one part of the chain of nucleotide units is specific and complementary to the nucleotide sequence of the detection probe used. The target can be natural or obtained from a reaction of enzymatic amplification in vitro, such as NASBA (Nucleic Acid Sequence-Based Amplification), PCR (Polymerase Chain Reaction) or any other technique known by a person skilled in the art. When the target sequence results from a reaction of enzymatic amplification in vitro, the sequences produced by this amplification are called "amplicons".

"Detection probe" means a nucleic acid sequence of 10 to 100 nucleotide units, notably from 10 to 50 nucleotide units and preferably from 25 to 40 nucleotides. This probe comprises a nucleotide fragment called the second fragment, for which at least one part of the chain of nucleotide units is specific and complementary to the nucleotide sequence of the target. This probe also comprises two other fragments called the first and third fragments, each having a closing sequence whose length is between 6 and 30 nucleotides and preferably between 6 and 15 nucleotides.

"First fragment" means a nucleotide sequence which can be complementary and of polarity suitable for said third segment when the latter is present.

"Second fragment" means a complementary nucleotide sequence of polarity suitable for the sequence of the target.

"Third fragment" means a complementary nucleotide sequence of polarity suitable for said first segment.

"Marker" means a molecule carried by a nucleotide. The bond between the marker and the nucleotide can be effected in various ways known by a person skilled in the art. Manual coupling is performed using markers bearing an activated group, typically a carboxyl or a thiol, which are coupled to a modified internal nucleotide bearing the corresponding reactive group (amine or thiol, for example), or to one end of the nucleotide strand modified with these same reactive groups. Automatic coupling is effected using phosphoroamidites bearing the marker, and then coupling takes place during automated synthesis of the nucleotide strand, either to one end of the strand, or to an internal position, depending on the type of phosphoroamidite used.

"Fluorophore" means a molecule that emits a fluorescence signal when it is excited by light of a suitable wavelength. The fluorophore can notably be a rhodamine or a derivative such as Texas Red, a fluorescein or a derivative, a fluorophore of the Alexa family such as Alexa532 and Alexa647, Alexa 405, Alexa 700, Alexa 680, or any other fluorophore that is suitable, depending on the measuring instrument used. The fluorophores available for the detection probes are very varied and are known by a person skilled in the art.

In the sense of the present invention, "fluorescein" means an aromatic chemical molecule that emits a fluorescence signal with a maximum emission at about 530 nm, when it is excited by light with a wavelength of about 495 nm.

"Fluorescence quencher" or "quencher" means a molecule that interferes with the fluorescence emitted by a fluorophore. This quencher can be selected from nonfluorescent aromatic molecules, to avoid parasitic emissions. Preferably, said quencher is a Dabsyl or a Dabsyl or a "Black hole Quencher™", which are nonfluorescent aromatic molecules that prevent the emission of fluorescence when they are physically near a fluorophore. The technique of fluorescence resonance energy transfer (FRET) can also be used, as described for example in Fluorescent Energy Transfer Nucleic Acid Probes, p. 4, Ed. V. V. Didenko, Humana Press 2006, ISSN 1064-3745. The quencher can also be selected from fluorescent molecules, for example TAMRA (carboxytetramethylrhodamine).

"Polarity" means the orientation of the nucleotide sequence, 5' to 3' or 3' to 5', relative to its complementary sequence. Thus, segments can be oriented:
  antiparallel: in this case the oligonucleotide is hybridized in the opposite direction to the complementary sequence. In the present invention, one of the embodiments has one of the closing sequences that is then constituted of inverted nucleotides so that the detection probe is of a circular shape when said closing sequence is hybridized to the other closing sequence.
  parallel: in this case, the oligonucleotide is hybridized in the same direction as the complementary sequence. In the present invention, one of the embodiments has one of the closing sequences that is then constituted of alpha nucleotides so that the detection probe is of a circular shape when said closing sequence is hybridized to the other closing sequence.

"Hybridization" means the process during which, in suitable conditions, two single-stranded nucleotide fragments having, wholly or partly, sequences that are sufficiently complementary, can form a double strand or "duplex" stabilized by hydrogen bonds between nucleic acid bases. The hybridization conditions are determined by the stringency and low salinity of the operating conditions. Hybridization is the more specific when it is carried out under greater stringency. Stringency is notably defined in relation to the base composition of a probe/target duplex, as well as by the degree of mispairing between two nucleic acids. Stringency can also be a function of the reaction variables, such as the concentration and type of ionic species present in the hybridization solution, the nature and concentration of denaturing agents and/or the hybridization temperature. The stringency of the conditions in which a hybridization reaction must be carried out will mainly depend on the hybridization probes used. All these data are well known and the appropriate conditions can be determined by a person skilled in the art.

"Alpha nucleotides" or "alpha-anomeric nucleotide" means deoxyribonucleotides or ribonucleotides with normatural alpha-anomeric configuration, in which the nitrogen-containing base carried by the anomeric carbon of the deoxyribose is positioned below the plane instead of being above the plane as in the case of beta nucleotides. The nitrogen-containing base of the alpha nucleotides can be a modified nucleic acid base, such as inosine, methyl-5-deoxycytidine, dimethylamino-5-deoxyuridine, deoxyuridine, diamino-2,6-purine, bromo-5-deoxyuridine or any other modified base permitting hybridization. The alpha nucleotides can also be modified at the level of the internucleotide bond, for example phosphorothioates, H-phosphonates, alkyl phosphonates or at the level of the backbone, for example 2'-O-alkyl ribose, PNA and LNA. Preferably, the alpha nucleotides are those described in application WO-A-88/04301.

"Inverted nucleotide" means deoxyribonucleotides or ribonucleotides having an orientation opposite to that of the sequence that contains them. Classically, synthesis taking place in the 3' to 5' direction, inverted nucleotides are introduced following or before the rest of the nucleotide strand, in the 5' to 3' direction. The inverted nucleotides and the rest of the strand are then joined together by a 5'-5' or 3'-3' bond. Reference may be made to Koga M. et al., J. Org. Chem., 1991, 56, 3757. The inverted nucleotides can optionally comprise at least one modified nucleotide, for example at least one nucleotide having a modified nucleic acid base, such as inosine, methyl-5-deoxycytidine, dimethylamino-5-deoxyuridine, deoxyuridine, diamino-2,6-purine, bromo-5-deoxyuridine or any other modified base permitting hybridization. The inverted nucleotides can also be modified at the level of the backbone for example PNAs, 2'-O-alkyl ribose and LNAs.

"End" means the starting point and the end point of synthesis of an oligonucleotide generally defined by the number carried by the free hydroxyls carried by the first or the last nucleoside, i.e. 3' or 5'. It is understood that with an appropriate choice of elongation units (phosphoroamidites of alpha or beta nucleosides, inverted or not), an oligonucleotide can be synthesized in the 3' to 5' direction or in the opposite direction, or the direction of elongation can even alternate during synthesis. This leads to oligonucleotides bearing 3'-5', 5'-3',3'-3' or 5'-5' ends.

In the sense of the present invention, "biological sample" means any sample that may contain nucleic acids. The latter can be extracted from tissues, blood, serum, saliva, a patient's circulating cells or can be from a food product, food-processing product or can be of environmental origin. Extraction is performed by any protocol known by a person skilled in the art, for example according to the method of isolation described in patent EP-B-0,369,063.

The accompanying figures are given as explanatory examples and are not in any way limiting. They will make it easier to understand the invention.

Figure 2:
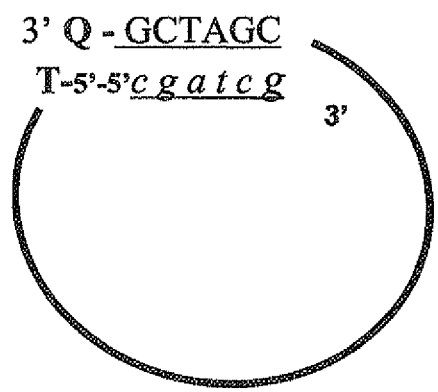
Figure 3A:
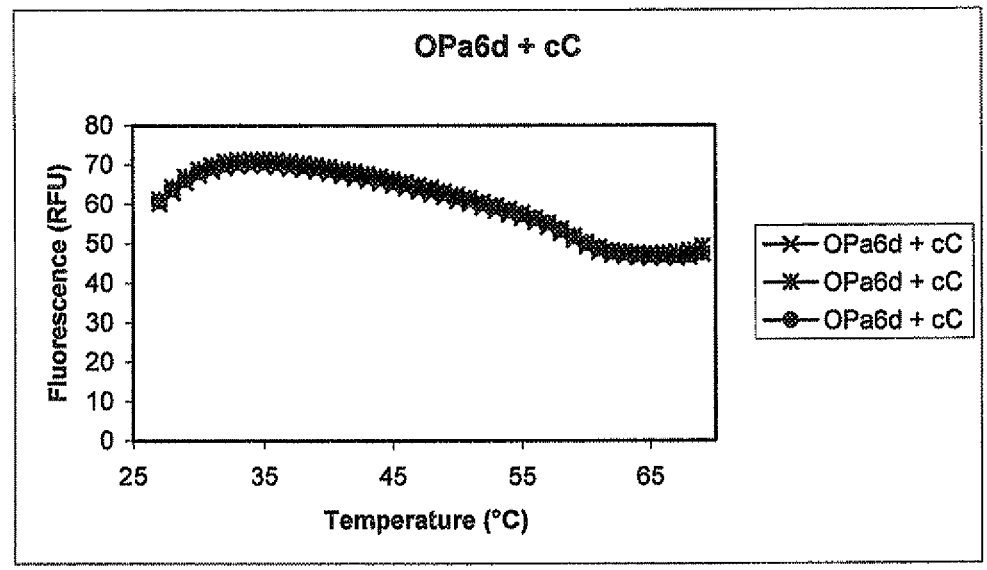
Figure 3B:
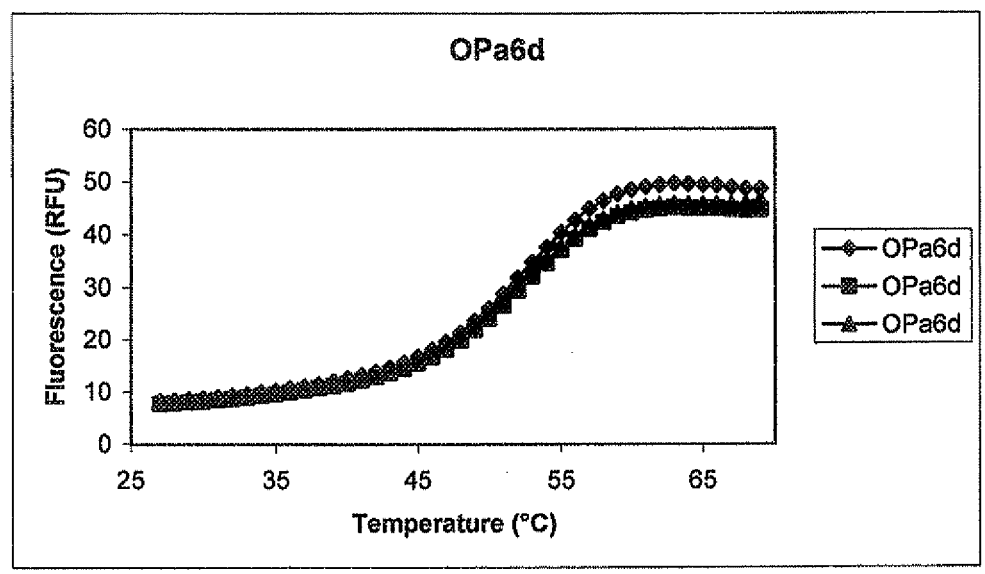

FIG. 1: Example of completely circular conformations of the probe according to the present invention.
T: dT-FAM, fluorophore
Nucleotide in lower case: alpha nucleotides
Q: fluorescence quencher FIG. 2: Example of completely circular conformations of the probe according to the present invention.
T: dT-FAM, fluorophore
Q: fluorescence quencher
Nucleotide in lower case: inverted nucleotides FIG. 3: Experiment of thermal denaturation of the probe according to the invention of the alpha type of the influenza B model, as described in example 1 (fluorescence emission in arbitrary unit (RFU for Relative Fluorescence Unit) as a function of the temperature measured in degrees Celsius (° C.)).
FIG. 3a: probe in the presence of its synthetic target.
FIG. 3b: probe alone without its target.

Figure 4A:
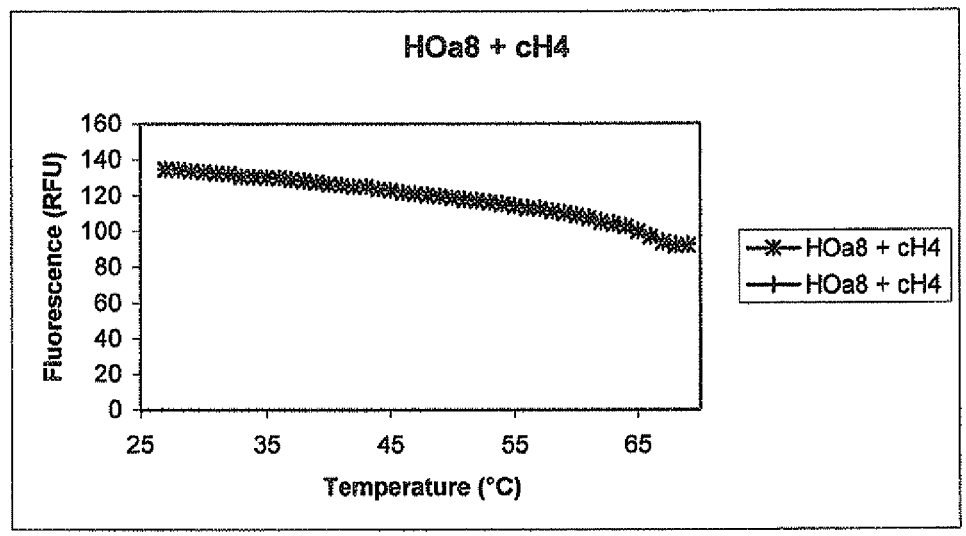
Figure 4B:
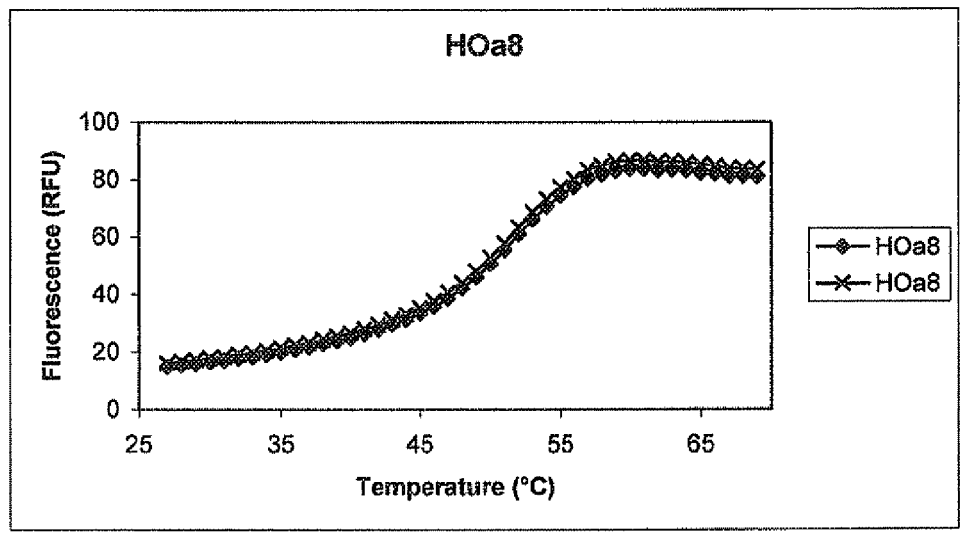

FIG. 4: Experiment of thermal denaturation of the probe according to the invention of the alpha type of the HIV model, as described in example 1 (fluorescence emission in arbitrary unit (RFU) as a function of the temperature (° C.)).
FIG. 4a: probe in the presence of its synthetic target.
FIG. 4b: probe alone without its target.

Figure 5A:
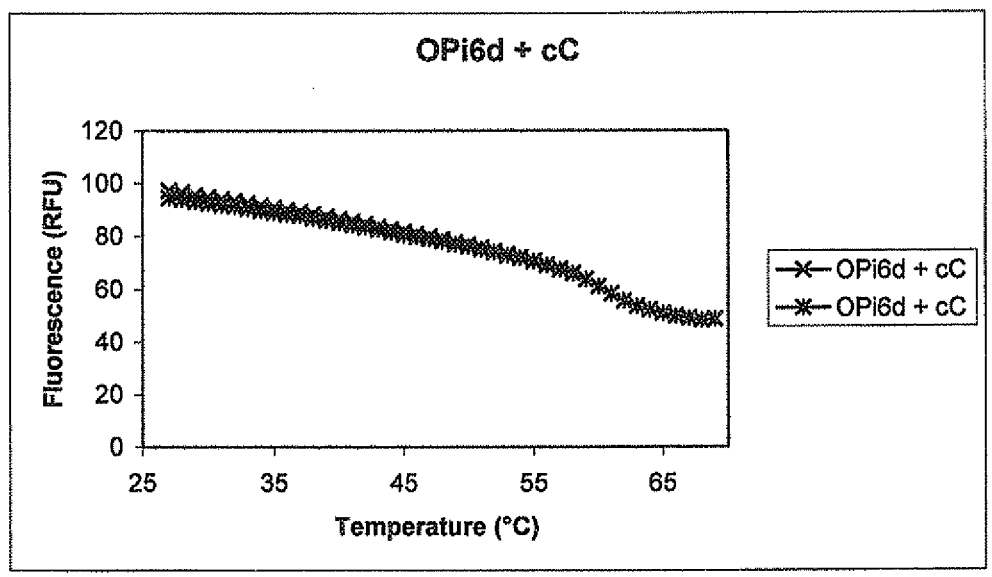
Figure 5B:
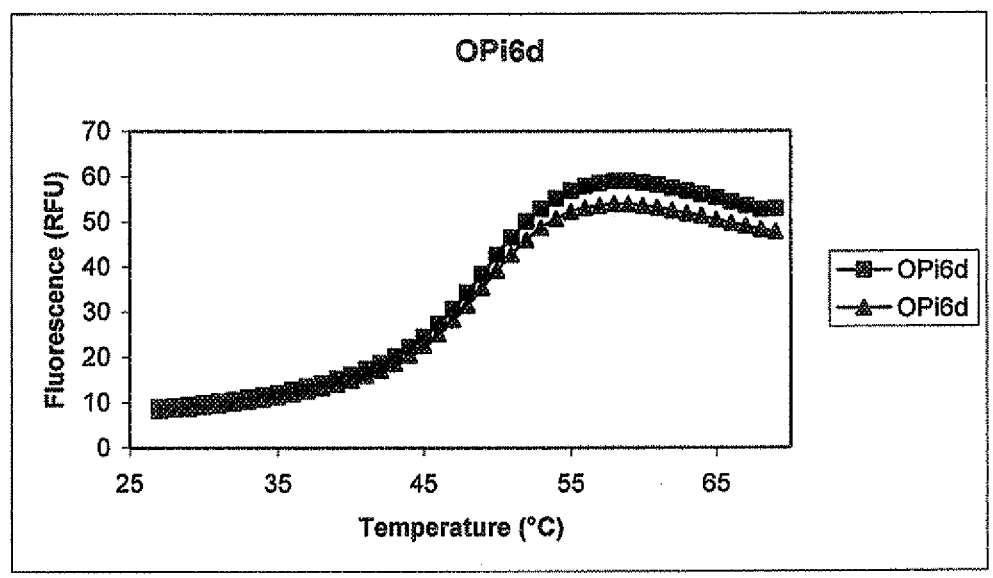

FIG. 5: Experiment of thermal denaturation of the probe according to the invention of the inverted type of the influenza B model, as described in example 2 (fluorescence emission in arbitrary unit (RFU) as a function of the temperature (° C.)).
FIG. 5a: probe in the presence of its synthetic target.
FIG. 5b: probe alone without its target.

Figure 6A:
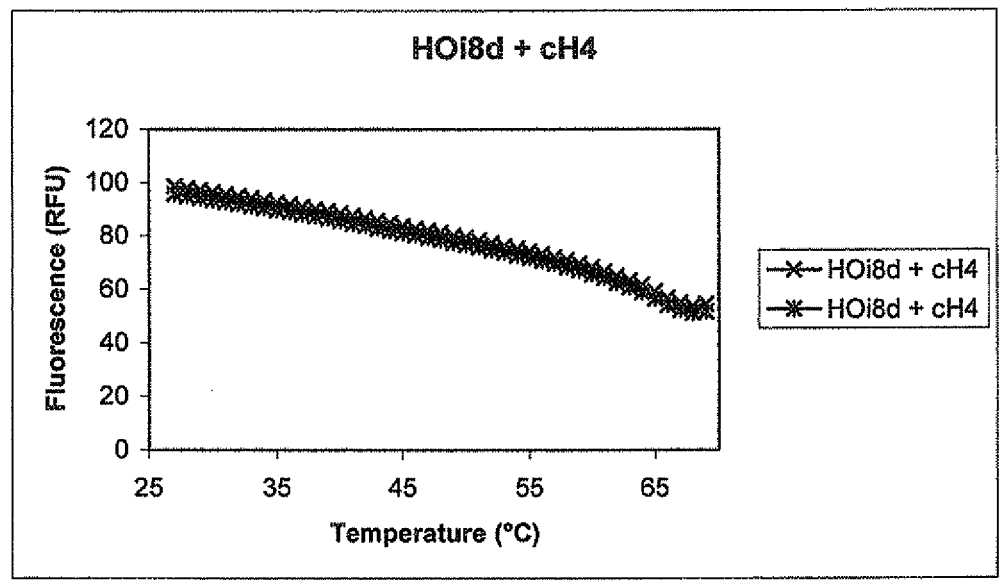
Figure 6B:
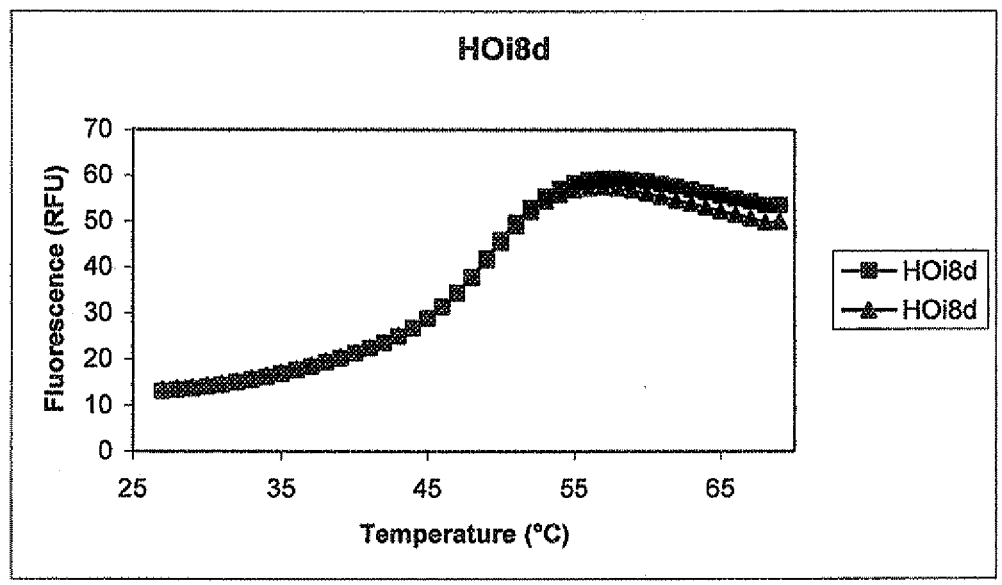

FIG. 6: Experiment of thermal denaturation of the probe according to the invention of the inverted type of the HIV model, as described in example 2 (fluorescence emission in arbitrary unit (RFU) as a function of the temperature (° C.)).
FIG. 6a: probe in the presence of its synthetic target.
FIG. 6b: probe alone without its target.

Figure 7:
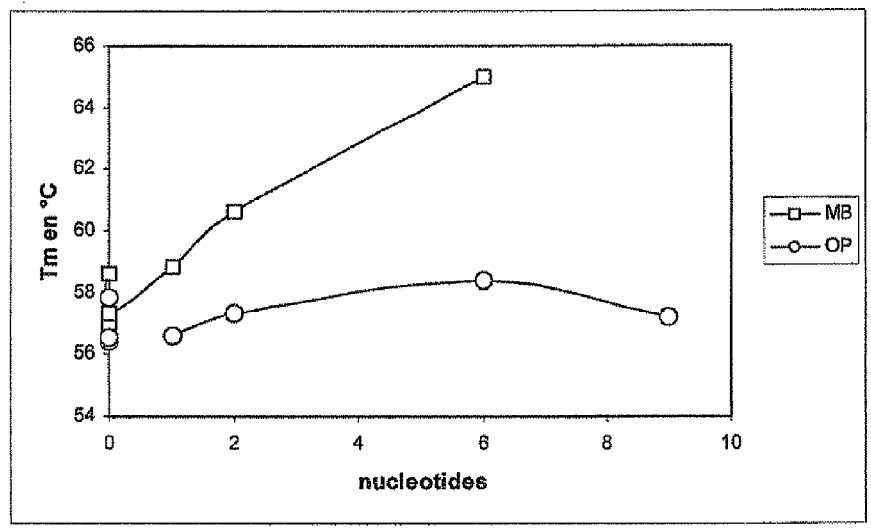

FIG. 7: Experiment for studying the specificity of hybridization of the probe of the alpha type according to the invention on the influenza B target model. The ordinate shows the value of the melting point measured in degrees Celsius (Tm for "melting temperature") as a function of the number of complementary nucleotides (abscissa) either of one of the strands of the "stem" part of the molecular beacon CpinfB (square symbol) or of one of the closing sequences of the probe according to the invention Opa6d (round symbol).

Figure 8:
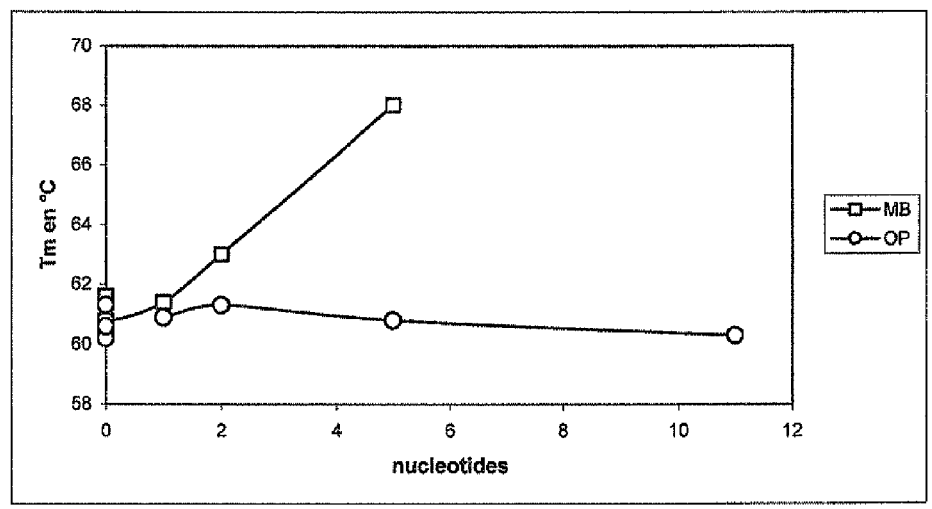

FIG. 8: Experiment for studying the specificity of hybridization of the probe of the alpha type according to the invention on the HIV-1A target model. The ordinate shows the value of the melting point (Tm) measured in degrees Celsius as a function of the number of complementary nucleotides (abscissa) either of one of the strands of the "stem" part of the molecular beacon HIV-1A (square symbol) or of one of the closing sequences of the probe according to the invention Hoa8 (round symbol).

Figure 9:
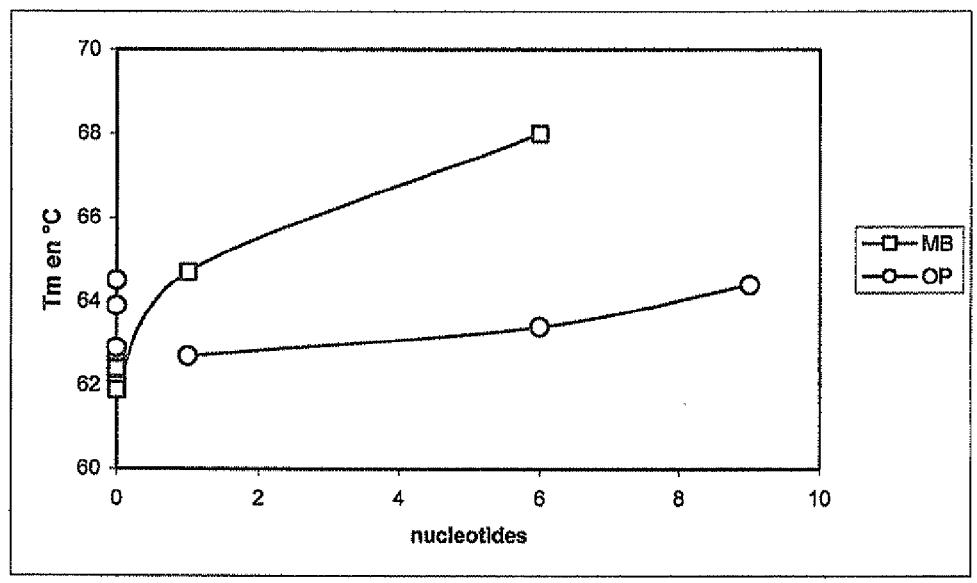

FIG. 9: Experiment for studying the specificity of hybridization of the probe according to the invention of the inverted type on the influenza B target model. The ordinate shows the value of the melting point (Tm) measured in degrees Celsius as a function of the number of complementary nucleotides (abscissa) either of one of the strands of the "stem" part of the molecular beacon CpinfB (square symbol) or of one of the closing sequences of the probe according to the invention Opi6d (round symbol).

Figure 10:
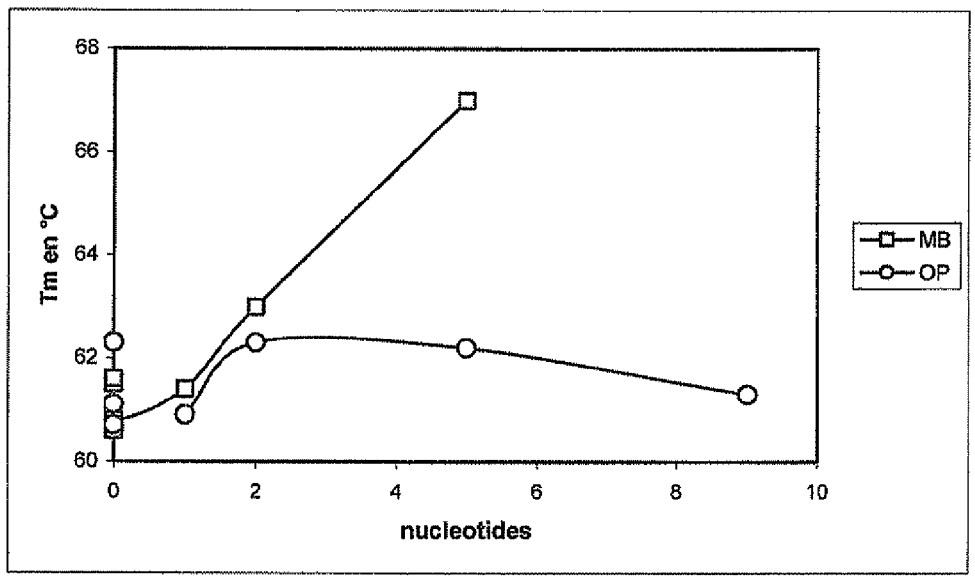

FIG. 10: Experiment for studying the specificity of hybridization of the probe according to the invention of the inverted type on the HIV-1A model. The ordinate shows the value of the melting point (Tm) measured in degrees Celsius as a function of the number of complementary nucleotides (abscissa) either of one of the strands of the "stem" part of the molecular beacon HIV-1A (square symbol) or of one of the closing sequences of the probe according to the invention Hoi8 (round symbol).

FIG. 11: Investigation of the undesirable premature opening of the molecular beacon probes and of the probes according to the invention in the presence of contaminants in the reaction mixture.

Figure 11A:
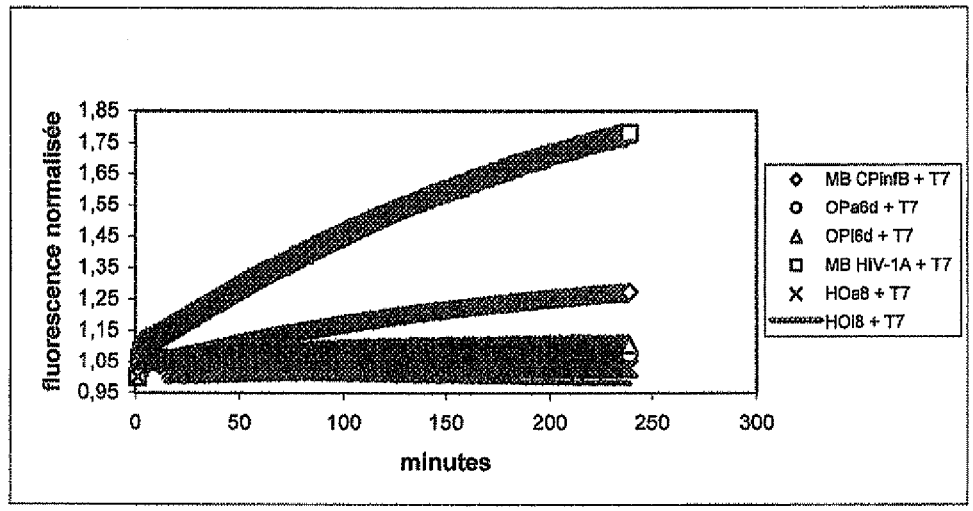

FIG. 11a: Measurement of the fluorescence signal of the probes (arbitrary unit, fluorescence standardized by dividing each value by the minimum initial value as a function of time (expressed in minutes)) in the presence of T7 RNA polymerase enzyme.

Figure 11B:
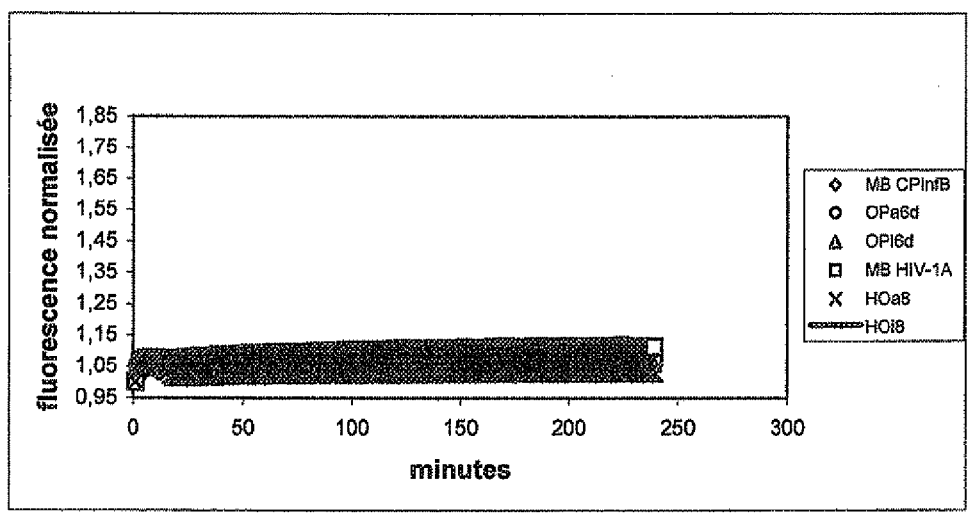

FIG. 11b: Measurement of the fluorescence signal of the probes (arbitrary unit, fluorescence standardized by dividing each value by the minimum initial value as a function of time (expressed in minutes)) in the absence of T7 RNA polymerase enzyme.

FIG. 12: Representation of the various structures used in the probes according to the invention.

Figure 12A:
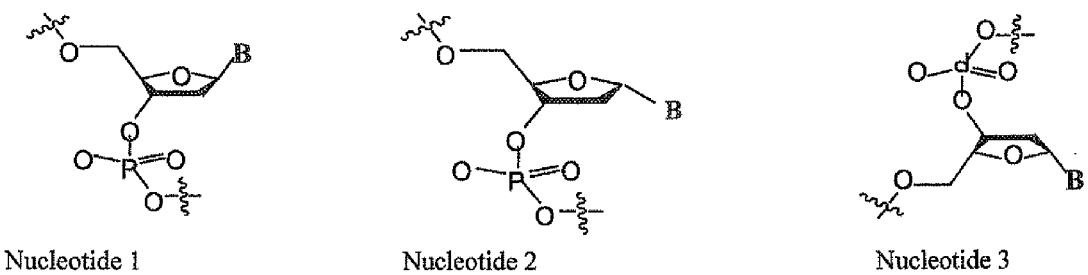

FIG. 12a: Structures of the different nucleotides used: Nucleotide 1=beta-anomeric nucleotide, Nucleotide 2=alpha-anomeric nucleotide, Nucleotide 3=inverted nucleotide.

Figure 12B:
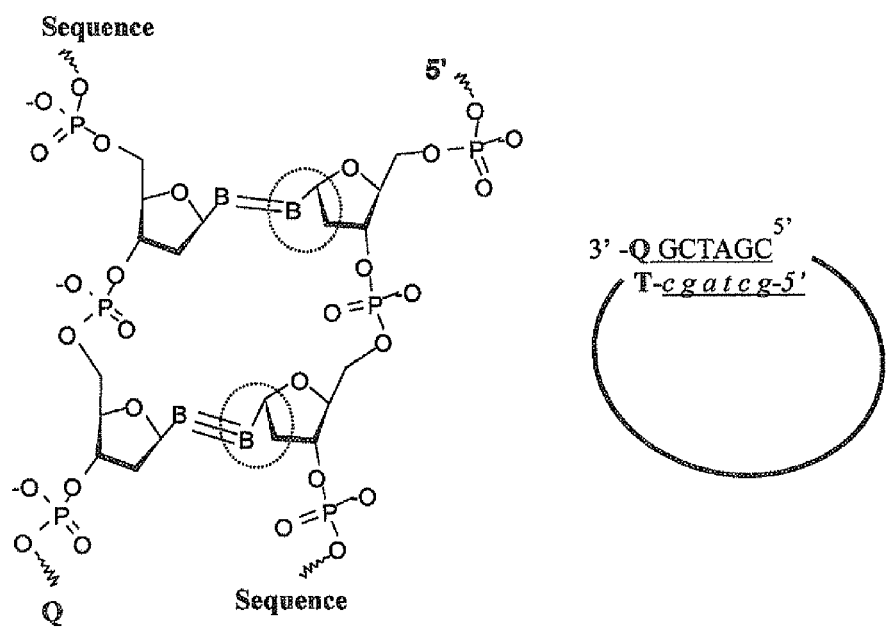

FIG. 12b: Example of hybridization of a closing sequence of the probes according to the invention when one of the strands is constituted of alpha nucleotides where: T is dT-FAM i.e. the fluorophore of this molecule; Q corresponds to the fluorescence quencher; the nucleotides in lower case are alpha nucleotides on the right-hand part of this diagram, whereas the circle drawn with a dotted line shows these same alpha-anomeric nucleotides on the left-hand part of this diagram; finally, the nucleotides in upper case, on the right-hand part of this diagram, are beta nucleotides, which, on the left-hand part, contain bases B which are not circled.

Figure 12C:
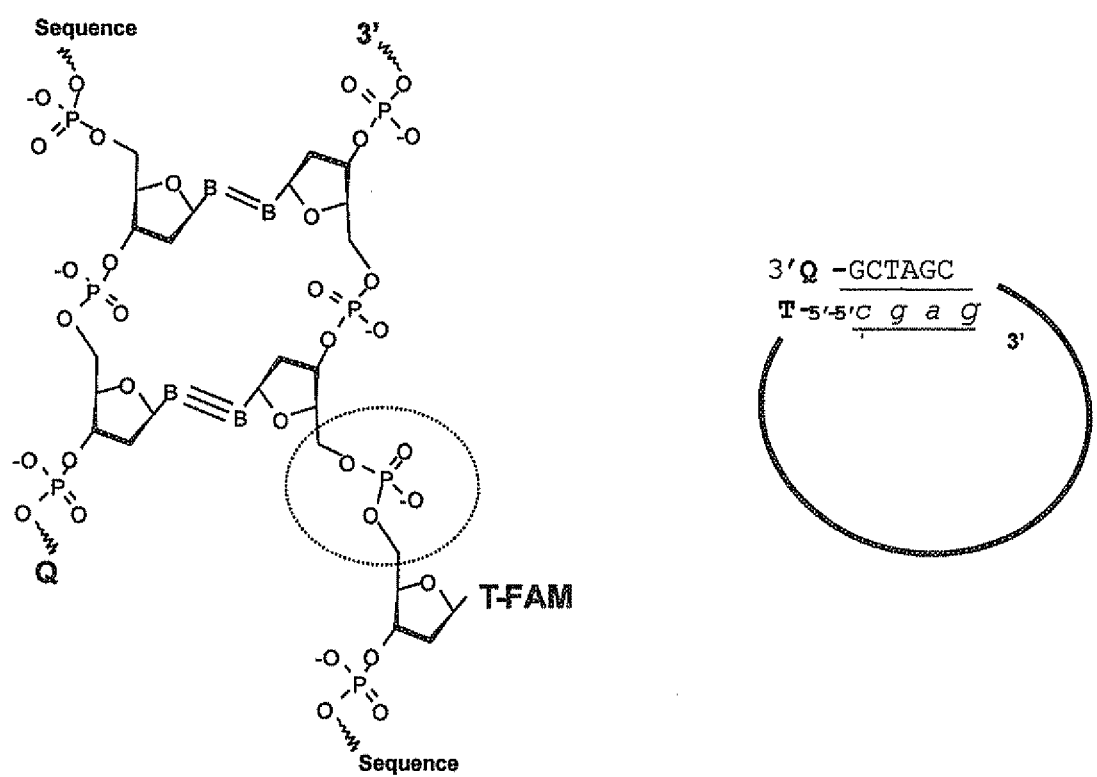

FIG. 12c: Example of hybridization of a closing sequence of the probes according to the invention when one of the strands is constituted of inverted nucleotides, where: T: dT-FAM, fluorophore; Q: fluorescence quencher; nucleotide in lower case: inverted nucleotides; circle drawn with dotted line shows the 5'-5' bond.

The probes according to the invention, the molecular beacon probes and the target nucleic acids, used in all of the examples given below, are synthesized following the synthesis procedure with phosphoroamidites, known by a person skilled in the art. The method of synthesis with phosphoroamidites was described by Beaucage and Lyer (Tetrahedron, 48, 223-2311, 1992). The reagents and phosphoroamidites are purchased commercially, notably from Eurogentec S. A. (Seraing, Belgium) and Glen Research (Sterling, Va., USA). The alpha phosphoroamidites, used for introducing the modified alpha nucleotides, are purchased from Chemgenes (Wilmington, Mass., USA, catalog No. ANP-1651, ANP-1652, ANP-1653, ANP-1654). The inverted phosphoroamidites, used for introducing the inverted nucleotides, are purchased from Glen Research (Sterling, Va., USA, catalog No. 10-0001, 10-0101, 10-0201, 10-0301). The oligonucleotides were purified by HPLC. Their purity was also monitored by HPLC analysis, and their identity was monitored by Maldi-TOF mass spectrometry.

The markers used in the probes according to the invention and the molecular beacons are:

Dabsyl fluorescence quencher (Glen Research, Cat. No. 20-5912), designated Da.

FAM (fluorescein-amine) fluorophore, Molecular Probes, Cat. No. C-2210

FAM (fluorescein-amine) fluorophore attached to a deoxythymine nucleotide (Glen Research, Cat. No. 10-1056), designated dT-FAM.

EXAMPLE 1

Investigation of Hybridization of the Probes According to the Invention of the Alpha Type of the Influenza B and HIV Models to their Target Sequence Objectives:

The objective of this experiment is to demonstrate that a probe according to the invention is capable of producing a fluorescence signal by hybridization in the presence of a complementary target sequence.

Experimental Design:

The probes used are as follows:

Influenza B Model-Opa6d probe (SEQ ID No. 1):
5'-gaccgtctg(dT-FAM)GGAGAAGACGTCCAAAAACTGGCAGA
C-3' Da HIV Model-HOa8 probe (SEQ ID No. 2):
5'-accctatctc(dT-FAM)CCATCAATGAGGAAGCTGCAGAATG
GGATAGAG-3' Da The nucleotide sequences underlined correspond to the closing sequences of the probes according to the invention.

The nucleotides written in lower case in the probes correspond to nucleotides of the alpha type.

The synthetic target sequences used are as follows:

Influenza B Model, target cC (SEQ ID No. 3):
5'-TTTAGTTTTTGGACGTCTTCTCCTTT-3'

HIV Model, target cH4 (SEQ ID No. 4):
5'-TTTACTCTATCCCATTCTGCAGCTTCCTCATTGATTTT-3'

The probes are introduced in a solution containing:
a basic kit diluent (bioMérieux B.V., Boxtel, the Netherlands, ref. 70352),
a probe at 0.1 micromolar concentration,
a synthetic target sequence at 1.25 micromolar concentration.

The final volume is 20 µl.

Negative controls are prepared using MilliQ ultrapure water instead of the target sequence.

This makes it possible to observe the behavior of the probe alone.

The solutions are heated to 65° C. in the fluorescence reader (EasyQ reader, bioMérieux B.V., Boxtel, The Netherlands) and left to cool for 5 hours. The fluorescence of each solution is measured at 520 nm throughout the cooling.

Results:

The results obtained are shown in FIGS. 3 and 4.

Probes Opa6 and Hoa8 in the presence of their respective synthetic target sequence (FIGS. 3a and 4a) present the expected fluorescence profile: at low temperature, the probe is hybridized to its target and the fluorophore is at a maximum distance from the quencher. The fluorescence is maximum. At high temperature, the probe/target double helix is destabilized, the probe becomes single-stranded and the distance between the fluorophore and the quencher decreases, causing a decrease in fluorescence. The thermal stability of the probe/target double helix is given by the value of "Tm-target". The Tm corresponds to the turning point of the curve fluorescence=f(temperature). Tm-target is calculated as the minimum of the first derivative of the curve. The probes Opa6 and Hoa8 have a Tm-target (see Table 1) that allows them to remain hybridized to their target at the temperature of the NASBA amplification reaction, 41° C., and thus produce a maximum fluorescence signal in the presence of its target sequence.

The Opa6d and Hoa8 probes alone (FIGS. 3b and 4b) present the expected fluorescence profile: at low temperature, the probe is structured in a circular shape and the fluorophore is very close to the quencher. The fluorescence emitted is very slight. At high temperature, the secondary structure is dissociated, the fluorophore moves away from the quencher and the fluorescence emission increases progressively and reaches a plateau when the secondary structure is completely denatured. The thermal stability of the secondary structure of the probe is given by the value of "Tm-probe", which corresponds to the turning point of the curve fluorescence=f(temperature). Tm-probe is calculated as the maximum of the first derivative of the curve. The Opa6d and Hoa8 probes have a Tm-probe (see Table 1) that allows them to remain closed at the temperature of the NASBA amplification reaction, 41° C., and thus produce a minimum of residual fluorescence in the absence of its target sequence.

The "open/closed ratio", also called "O/C ratio", makes it possible to measure the level of signal produced by a probe in the presence of its target at 41° C. It is calculated as the ratio of the signal produced by the probe in the presence of its target sequence to the residual signal produced by the probe alone.

Table 1 presents the values of Tm-probe, Tm-target and O/C ratio obtained with the probes described in this example.

TABLE 1

Values of Tm-probe, Tm-target and O/C ratio

| Probe | Tm-probe (° C.) | Tm-target (° C.) | O/C ratio |
|---|---|---|---|
| OPa6d (SEQ ID No. 1) | 51.8 | 57.7 | 5.4 |
| HOa8 (SEQ ID No. 2) | 51.0 | 64.5 | 4.5 |

Conclusions:

The probes according to the invention of the alpha type, influenza B and HIV models, alone in solution, form a secondary structure stable at 41° C., producing extinction of the fluorescence signal due to the proximity of the fluorophore and the quencher.

When they are in solution in the presence of their synthetic target sequence, they hybridize to their synthetic target sequences, producing a measurable fluorescence signal.

EXAMPLE 2

Investigation of Hybridization of the Probes According to the Invention of the Inverted Type of the Influenza B and HIV Models to their Target Sequence Objectives:

The objective of this experiment is to demonstrate that a probe modified according to the invention is capable of producing a fluorescence signal by hybridization in the presence of a complementary target sequence.

Experimental Design:

The probes used are as follows:

```
Influenza B Model-probe Opi6d (SEQ ID No. 5):
5'-Da-GGAGAAGACGTCCAAAAACTGGCAGA-3'-(dT-FAM)-
3'-cctcttctg-5'

HIV Model-probe HOi8d (SEQ ID No. 6):
5'-Da-CCATCAATGAGGAAGCTGCAGAATGGGATAGAG-3'-
(dT-FAM)-3'-ggtagttactc-5'
```

The sequences underlined correspond to the closing sequences of the probes according to the invention.

The nucleotides written in lower case and in bold in the probes correspond to inverted nucleotides.

The synthetic target sequences used are as follows:

```
Influenza B Model, target cC (SEQ ID No. 3):
5'-TTTAGTTTTTGGACGTCTTCTCCTTT-3'

HIV Model, target cH4 (SEQ ID No. 4):
5'-TTTACTCTATCCCATTCTGCAGCTTCCTCATTGATTTT-3'
```

The probes are introduced in a solution containing:
a basic kit diluent (bioMérieux B.V., Boxtel, The Netherlands, ref. 70352),
a probe at 0.1 micromolar concentration,
a synthetic target sequence at 1.25 micromolar concentration.

The final volume is 20 µl.

Negative controls are prepared using MilliQ ultrapure water instead of the target sequence. This makes it possible to observe the behavior of the probe alone.

The solutions are heated to 65° C. in the fluorescence reader (EasyQ reader, bioMérieux B.V., Boxtel, the Netherlands) and left to cool for 5 hours. The fluorescence of each solution is measured at 520 nm throughout the cooling. The results are expressed in the form of a graph of temperature versus fluorescence.

Results:

The results obtained are shown in FIGS. 5 and 6.

The Opi6 and Hoi8d probes in the presence of their respective synthetic target sequence (FIGS. 5a and 6a) present the expected fluorescence profile: at low temperature, the probe is hybridized to its target forming a duplex that is sufficiently rigid to move the fluorophore away from the quencher. In this duplex, the two molecules are a maximum distance apart. The fluorescence emitted is maximum.

At high temperature, the probe/target double helix is dissociated, and the probe then becomes single-stranded. In this case, even if the secondary structure within this probe is dissociated, the distance between the fluorophore and the quencher is less than that in the probe/target duplex because of the flexibility of the denatured probe. This causes a decrease in fluorescence by extinction. The thermal stability of the probe/target double helix is given by the value of "Tm-target", which corresponds to the turning point of the curve fluorescence=f(temperature). Tm-target is calculated as the minimum of the first derivative of the curve. The Opi6 and Hoi8d probes have a Tm-target (see Table 2) that allows them to remain hybridized to their target at the temperature of the NASBA amplification reaction, 41° C., and thus produce a maximum fluorescence signal in the presence of their target sequence.

The Opi6d and Hoi8d probes alone (FIGS. 5b and 6b) present the expected fluorescence profile: at low temperature, the probe is structured in a circular shape and the fluorophore is very close to the quencher. The fluorescence emitted is very slight. At high temperature, the secondary structure is dissociated, the fluorophore moves away from the quencher and the fluorescence emission increases progressively and reaches a plateau when the secondary structure is completely denatured. The thermal stability of the secondary structure of the probe is given by the value of "Tm-probe", which corresponds to the turning point of the curve. Tm-probe is calculated as the maximum of the first derivative of the curve fluorescence f(temperature). The Opi6d and Hoi8d probes have a Tm-probe (see Table 2) that allows them to remain closed at the temperature of the NASBA amplification reaction, 41° C., and thus produce a minimum of residual fluorescence in the absence of its target sequence.

The "open/closed ratio", also called "O/C ratio", makes it possible to measure the level of signal produced by a probe in the presence of its target at 41° C. It is calculated as the ratio of the signal produced by the probe in the presence of its target sequence to the residual signal produced by the probe alone.

Table 2 presents all the values of Tm-probe, Tm-target and O/C ratio obtained with the probes described in this example.

TABLE 2

Values of Tm-probe, Tm-target and O/C ratio

| Probe | Tm-probe (° C.) | Tm-target (° C.) | O/C ratio |
|---|---|---|---|
| OPi6d (SEQ ID No. 5) | 48.5 | 59.7 | 5.3 |
| HOi8d (SEQ ID No. 6) | 48.6 | 64.0 | 3.7 |

Conclusions:

The probes according to the invention of the inverted type of the influenza B and HIV models, alone in solution, form a secondary structure stable at 41° C., producing extinction of the fluorescence signal due to the proximity of the fluorophore and the quencher. When they are in solution in the presence of their synthetic target sequence, they hybridize to their synthetic target sequences, producing a measurable fluorescence signal.

EXAMPLE 3

Investigation of Real-Time Detection During NASBA Amplification of the Target Influenza B by the Probes According to the Invention of the Alpha Type Objectives:

The objective of this experiment is to demonstrate that a probe according to the invention is capable of detecting its target sequence in real time during NASBA amplification.

Experimental Design:

The target sequence of the amplification is an RNA with a length of 212 nucleotides, synthesized by transcription from a plasmid according to an in vitro transcription technique known by a person skilled in the art. The sequence of this RNA corresponds to a sequence of the genome of the influenza B virus.

The primers and probes used are as follows:
Primers:

```
P1 (SEQ ID No. 7):
5'-AATTCTAATACGACTCACTATAGGGGAGCTCTGCTTTAGCAC
TTCCA-3'

P2 (SEQ ID No. 8):
5'-GAGAAATGCAGATGGTCTCAGCTA-3'

Opa6d Probe (SEQ ID No. 1):
5'-gaccgtctg(dT-FAM)GGAGAAGACGTCCAAAAACTGGCAG
AC-3' Da
```

The segment in italics of primer P1 corresponds to the sequence of the promoter recognized by the T7 RNA polymerase enzyme, necessary for NASBA in vitro enzymatic amplification.

The segments underlined correspond to the closing sequences of the probes according to the invention.

The nucleotides written in lower case in the Opa6d probe correspond to nucleotides of the alpha type.

The segment at 3' of primer P1 is complementary to a sequence of the target RNA. The sequence of primer P2 is the same as a sequence of the target RNA located on the 5' end of the complementary sequence of primer P1. The NASBA amplification reaction will generate a multitude of copies of an RNA sequence, called "amplicon", whose sequence corresponds to the complementary sequence of the target RNA, in the segment between the hybridization sequence of primer P1 and the sequence equal to the sequence of primer P2. The probes according to the invention include a recognition sequence that will hybridize to the amplicons generated by the NASBA amplification reaction. Accordingly, the signal produced by the probe is only detected when the target RNA sequence is present in the reaction mixture and is amplified by NASBA with the chosen primers.

The NASBA amplification reaction is carried out using the "NASBA basic kit" reagents (bioMérieux B.V., Boxtel, the Netherlands, ref. 60079136 & 60085192) and in the conditions specified by the manufacturer. Each amplification tube contains a final volume of 20 µl, which is composed as follows:

8.64 µl of the "NASBA basic kit" reagents in the proportions specified by the manufacturer,
0.4 µl of primer P1 at 10 µM,
0.4 µl of primer P2 at 10 µM,
0.16 µl of the Opa6d probe at 10 µM,
5 µl of the RNA target at a concentration sufficient to obtain a final concentration of 5, 50, 500 or 5000 copies per reaction tube.

In all cases, a negative control is prepared which contains "DNase/RNase free" water (catalog No. 32739, ACROS). All the experiments are performed in duplicate.

After a stage of denaturation of 5 minutes at 65° C. then incubation for 2 minutes at 41° C., 5 µl of the "enzyme mix" reagent (1 "enzyme" accusphere 60085111 to 45 µl of "enzyme" diluent 60085192, part of the "NASBA basic kit") is added to the reaction mixture. The reaction mixture is then introduced into the fluorescence reader, the temperature of which has been set to 41° C., and the reaction is monitored by means of the Director 2.0 software of the fluorescence reader (EasyQ reader, bioMérieux B.V, Boxtel, the Netherlands), with reading of the fluorescence emitted by the FAM fluorophore for 90 minutes at 520 nm.

At the end of the reaction, a graphic detection profile is obtained for each tube, with the numerical values of "Alpha3" and "MSR". The value "Alpha3" is "the primer exhaustion time" as described in the article of Weusten et al. (Nucleic Acids Research 2002, vol. 30, No. 6, e26). This value corresponds to the time at which the increase in the fluorescence signal begins to be detectable. The quicker and therefore more efficient the amplification, the shorter the Alpha3 value.

The value "MSR" is the "Maximum signal ratio". This value corresponds to the ratio of the fluorescence value read at the end of the amplification reaction to the theoretical final fluorescence value extrapolated to the initial values, before the signal began to increase. This value is the signal level acquired by the probe, and must be greater than 1 for the signal to be considered positive. These two values are calculated and displayed automatically by the software of the EasyQ reader for each sample.

Results:

The results of detection in NASBA in real time are not shown but are available if required. It can be seen that the limit of detection is at 5 copies of target transcript. The positive samples produce a detectable signal with an optimum "MSR" of 4.47 and a value of "Alpha3" between 23 and 31 minutes.

Conclusions:

The Opa6d probe according to the invention is capable of emitting a detectable fluorescence signal in the presence of its target in solution, characterized by an optimum signal level of 4.47 ("MSR"). The value of "Alpha3", which marks the time at which the signal becomes detectable, is between 23 and 31 minutes. "Alpha3" is proportional to the amount of target present, which offers the possibility of quantifying the target on the basis of this value.

EXAMPLE 4

Investigation of Real-Time Detection During NASBA Amplification of the Target Influenza B by the Probes According to the Invention of the Inverted Type Objectives:

The objective of this experiment is to demonstrate that a probe according to the invention is capable of detecting its target sequence in real time during NASBA amplification.

Experimental Design

The target sequence of the amplification is an RNA with a length of 212 nucleotides, synthesized by transcription from a plasmid according to an in vitro transcription technique known by a person skilled in the art. The sequence of this RNA corresponds to a sequence of the genome of the influenza B virus.

The primers and probes used are as follows:
Primers:

```
P1 (SEQ ID No. 7):
5'-AATTCTAATACGACTCACTATAGGGGAGCTCTGCTTTAGCAC
TTCCA-3'

P2 (SEQ ID No. 8):
5'-GAGAAATGCAGATGGTCTCAGCTA-3'

Opi6d Probe (SEQ ID No. 5):
5'-Da-GGAGAAGACGTCCAAAAACTGGCAGA-(dT-FAM)-3'-
3'-cctcttctg-5'
```

The segments underlined correspond to the closing sequences of the probes according to the invention.

The segment in italics of primer P1 corresponds to the sequence of the promoter recognized by the T7 RNA polymerase enzyme, necessary for NASBA in vitro enzymatic amplification. The nucleotides written in lower case and in bold in the Opi6d probe correspond to inverted nucleotides.

The segment at 3' of primer P1 is complementary to a sequence of the target RNA. The sequence of primer P2 is the same as a sequence of the target RNA located on the 5' end of the complementary sequence of primer P1. The NASBA amplification reaction will generate a multitude of copies of an RNA sequence, called "amplicon", whose sequence corresponds to the complementary sequence of the target RNA, in the segment between the hybridization sequence of primer P1 and the sequence equal to the sequence of primer P2. The probes according to the invention include a recognition sequence that will hybridize to the amplicons generated by the NASBA amplification reaction. Accordingly, the signal produced by the probe is only detected when the target RNA sequence is present in the reaction mixture and is amplified by NASBA with the chosen primers.

The NASBA amplification reaction is carried out using the "NASBA basic kit" reagents (bioMérieux B.V., Boxtel, the Netherlands, ref.: 60079136 and 60085192) and in the conditions specified by the manufacturer. Each amplification tube contains a final volume of 20 µl, which is composed as follows:

8.64 µl of the "NASBA basic kit" reagents in the proportions specified by the manufacturer,
0.4 µl of primer P3 at 10 µM,
0.4 µl of primer P2 at 10 µM,
0.16 µl of probe Opi6d at 10 µM,
5 µl of target RNA at a concentration sufficient to obtain a final concentration of 5, 50, 500 or 5000 copies per reaction tube.

In all cases, a negative control is prepared which contains "DNase/RNase free" water (catalog No. 32739, ACROS).

After a stage of denaturation of 5 minutes at 65° C. and then incubation for 2 minutes at 41° C., 5 µl of the "enzyme mix" reagent (1 "enzyme" accusphere ref. 60085111 to 45 µl of "enzyme" diluent ref. 60085192, part of the "NASBA basic kit") is added to the reaction mixture. The reaction mixture is then introduced into the fluorescence reader, the temperature of which has been set to 41° C. and the reaction is monitored with the Director 2.0 software of the fluorescence reader (EasyQ reader, bioMérieux B.V., Boxtel, the Netherlands), with reading of fluorescence of the FAM fluorophore for 90 minutes at 520 nm.

At the end of the reaction, a graphic detection profile is obtained for each tube, together with the numerical values of "Alpha3" and "MSR".

Results:

The results of detection in NASBA in real time are not shown but are available if required. It can be seen that the limit of detection is at 5 copies of target transcript. The positive samples produce a detectable signal with an optimum "MSR" of 3.88 and a value of "Alpha3" between 18 and 26 minutes.

Conclusions:

The Opi6d probe according to the invention is capable of emitting a detectable fluorescence signal in the presence of its target in solution, characterized by an optimum signal level of 3.88 ("MSR"). The value of "Alpha3", which marks the time at which the signal becomes detectable, is between 18 and 26 minutes. "Alpha3" is proportional to the amount of target present, which offers the possibility of quantifying the target on the basis of this value.

EXAMPLE 5

Investigation of Real-Time Detection During NASBA Amplification of the HIV Target by the Probes According to the Invention of the Alpha Type Objectives:

The objective of this experiment is to demonstrate that a probe according to the invention is capable of detecting its target sequence in real time during NASBA amplification.

Experimental Design:

The target sequence of the amplification is an RNA with a length of 212 nucleotides, synthesized by transcription from a plasmid according to an in vitro transcription technique known by a person skilled in the art. The sequence of this RNA corresponds to a sequence of the genome of the "HIV" human immunodeficiency virus.

The primers and probes used are as follows:
Primers:

```
P3 (SEQ ID No. 9):
5'-AATTCTAATACGACTCACTATAGGGTGCTATGTCACTTCCCCTT
GGTTCTCTCA-3'

P4 (SEQ ID No. 10):
5'- AGTGGGGGGACATCAAGCAGCCATGCAAA-3'

Hoa6 Probe (SEQ ID No. 11):
5'-accctatcc-(dT-FAM)-ATCAATGAGGAAGCTGCAGAATGGG
ATAGG-3'-Da
```

The segments underlined correspond to the closing sequences of the probes according to the invention.

The segment in italics of primer P3 corresponds to the sequence of the promoter recognized by the T7 RNA polymerase enzyme, necessary for NASBA in vitro enzymatic amplification. The nucleotides written in lower case in probe Hoa6 correspond to alpha nucleotides.

The segment at 3' of primer P3 is complementary to a sequence of the target RNA. The sequence of primer P4 is the same as a sequence of the target RNA located on the 5' end of the complementary sequence of primer P3. The NASBA amplification reaction will generate a multitude of copies of an RNA sequence, called "amplicon", whose sequence corresponds to the complementary sequence of the target RNA, in the segment between the hybridization sequence of primer P3 and the sequence equal to the sequence of primer P4. The probes according to the invention include a recognition sequence that will hybridize to the amplicons generated by the NASBA amplification reaction. Accordingly, the signal produced by the probe is only detected when the target RNA sequence is present in the reaction mixture and is amplified by NASBA with the chosen primers.

The NASBA amplification reaction is carried out using the "NASBA basic kit" reagents (bioMérieux B.V., Boxtel, the Netherlands, ref. 60079136 and 60085192) and in the conditions specified by the manufacturer. Each amplification tube contains a final volume of which is composed as follows:

8.64 µl of the "NASBA basic kit" reagents in the proportions specified by the manufacturer,
0.4 µl of primer P3 at 10 µM,
0.4 µl of primer P4 at 10 µM,
0.16 µl of probe Hoa6 at 10 µM,
5 µl of target RNA at a concentration sufficient to obtain a final concentration of 5, 50, 500 or 5000 copies per reaction tube.

In all cases, a negative control is prepared which contains "DNase/RNase free" water (catalog No. 32739, ACROS).

After a stage of denaturation of 5 minutes at 65° C. and then incubation for 2 minutes at 41° C., 5 µl of the "enzyme mix" reagent (1 "enzyme" accusphere ref. 60085111 to 45 µl of "enzyme" diluent ref. 60085192, part of the "NASBA basic kit") is added to the reaction mixture. The reaction mixture is then introduced into the fluorescence reader, the temperature of which has been set to 41° C. and the reaction is monitored with the Director 2.0 software of the fluorescence reader (EasyQ reader, bioMérieux B.V., Boxtel, the Netherlands), with reading of fluorescence of the FAM fluorophore for 90 minutes at 520 nm.

At the end of the reaction, a graphic detection profile is obtained for each tube, together with the numerical values of "Alpha3" and "MSR".

Results:

The results of detection in NASBA in real time are not shown but are available if required. It can be seen that the limit of detection is equal to or less than 5 copies of target transcript. The positive samples produce a detectable signal with an optimum "MSR" of 2.53 and a value of "Alpha3" between 14 and 22 minutes.

Conclusions:

The Hoa6 probe according to the invention is capable of emitting a detectable fluorescence signal in the presence of its target in solution, characterized by an optimum signal level of 2.53 ("MSR"). The value of "Alpha3", which marks the time at which the signal becomes detectable, is between 14 and 22 minutes. "Alpha3" is proportional to the amount of target present, which offers the possibility of quantifying the target on the basis of this value.

EXAMPLE 6

Investigation of Real-Time Detection During NASBA Amplification of the HIV Target by the Probes According to the Invention of the Inverted Type Objectives:

The objective of this experiment is to demonstrate that a probe according to the invention is capable of detecting its target sequence in real time during NASBA amplification.

Experimental Design:

The target sequence of the amplification is an RNA with a length of 212 nucleotides, synthesized by transcription from a plasmid according to an in vitro transcription technique known by a person skilled in the art. The sequence of this RNA corresponds to a sequence of the genome of the "HIV" human immunodeficiency virus.

The primers and probes used are as follows:

Primers:

```
P3 (SEQ ID No. 9):
5'-AATTCTAATACGACTCACTATAGGGTGCTATGTCACTTCCCCTT
GGTTCTCTCA-3'

P4 (SEQ ID No. 10):
5'-AGTGGGGGGACATCAAGCAGCCATGCAAA-3'

Hoi6d Probe (SEQ ID No. 12):
5'-Da-CCATCAATGAGGAAGCTGCAGAATGGGATAGG-3'-
(dT-FAM)3'-ggtagttact-5'
```

The segments underlined correspond to the closing sequences of the probes according to the invention.

The nucleotides written in lower case and in bold in the probes correspond to inverted nucleotides.

The segment in italics of primer P3 corresponds to the sequence of the promoter recognized by the T7 RNA polymerase enzyme, necessary for NASBA in vitro enzymatic amplification. The nucleotides written in lower case and in bold in the Hoi6d probe correspond to inverted nucleotides.

The segment at 3' of primer P3 is complementary to a sequence of the target RNA. The sequence of primer P4 is the same as a sequence of the target RNA located on the 5' end of the complementary sequence of primer P3. The NASBA amplification reaction will generate a multitude of copies of an RNA sequence, called "amplicon", whose sequence corresponds to the complementary sequence of the target RNA, in the segment between the hybridization sequence of primer P3 and the sequence equal to the sequence of primer P4. The probes according to the invention include a recognition sequence that will hybridize to the amplicons generated by the NASBA amplification reaction. Accordingly, the signal produced by the probe is only detected when the target RNA sequence is present in the reaction mixture and is amplified by NASBA with the chosen primers.

The NASBA amplification reaction is carried out using the "NASBA basic kit" reagents (bioMérieux Boxtel, the Netherlands, ref. 60079136 and 60085192) and in the conditions specified by the manufacturer. Each amplification tube contains a final volume of which is composed as follows:

8.64 µl of the "NASBA basic kit" reagents in the proportions specified by the manufacturer,
0.4 µl of primer P3 at 10 µM,
0.4 µl of primer P4 at 10 µM,
0.16 µl of the Hoi6d probe at 10 µM,
5 µl of target RNA at a concentration sufficient to obtain a final concentration of 5, 50, 500 or 5000 copies per reaction tube.

In all cases, a negative control is prepared which contains "DNase/RNase free" water (catalog No. 32739, ACROS).

After a stage of denaturation of 5 minutes at 65° C. and then incubation for 2 minutes at 41° C., 5 µl of the "enzyme mix" reagent (1 "enzyme" accusphere ref. 60085111 to 45 µl of "enzyme" diluent ref. 60085192, part of the "NASBA basic kit") is added to the reaction mixture. The reaction mixture is then introduced into the fluorescence reader, the temperature of which has been set to 41° C. and the reaction is monitored with the Director 2.0 software of the fluorescence reader (EasyQ reader, bioMérieux B.V., Boxtel, the Netherlands), with reading of fluorescence of the FAM fluorophore for 90 minutes at 520 nm.

At the end of the reaction, a graphic detection profile is obtained for each tube with the numerical values of "Alpha3" and "MSR".

Results:

The results of detection in NASBA in real time are not shown but are available if required. It can be seen that the limit of detection is equal to or less than 5 copies of target transcript. The positive samples produce a detectable signal with an optimum "MSR" of 2.03 and a value of "Alpha3" between 15 and 21 minutes.

Conclusions:

The Hoi6d probe according to the invention is capable of emitting a detectable fluorescence signal in the presence of its target in solution, characterized by an optimum signal level of 2.03 ("MSR"). The value of "Alpha3", which marks the time at which the signal becomes detectable, is between 15 and 21 minutes, "Alpha3" is proportional to the amount of target present, which offers the possibility of quantifying the target on the basis of this value.

EXAMPLE 7

Investigation of the Specificity of the Probes According to the Invention on the Influenza B Model Objectives:

The specificity of a probe is its capacity to recognize only its target, and thus differentiate it from a target comprising for example mispairings or deletions. Molecular beacons are currently the most specific molecular probes since they permit the differentiation of two targets differing by just one nucleotide. The objective of this experiment is to show the level of specificity of the probes according to the invention, in comparison with the molecular beacon probe that contains the same recognition sequence.

Experimental Design:

The probes used are as follows:

```
Molecular beacon CP InfB (SEQ ID No. 13):
5'-(FAM)-CGATCGGGAGAAGACGTCCAAAAACTCGATCG-3'Da Opa6 Probe (SEQ ID No. 14):
5'-gagcgtagc(dT-FAM)GGAGAAGACGTCCAAAAACTCGC
ATCG-3' Da Opa5 Probe (SEQ ID No. 15):
5'-gagctagc(dT-FAM)GGAGAAGACGTCCAAAAACTCGATC
G-3' Da Opi4 Probe (SEQ ID No. 16):
3'-gagctagc-5'-5'-(dT-FAM)GGAGAAGACGTCCAAAAACTC
GATCG-3' Da
```

```
Opi3 Probe (SEQ ID No. 17):
3'-gctagcc-5'-5'-(dT-FAM)GGAGAAGACGTCCAAAAACTCGA
TCGG-3' Da
```

The segments underlined correspond to the closing sequences of the probes according to the invention and to the sequences of the strands forming the "stem" part of the molecular beacon. The nucleotides written in lower case in the probes correspond to nucleotides of the alpha type.

The nucleotides written in lower case and in bold in the probes correspond to inverted nucleotides.

The synthetic target sequences used are as follows:

```
Target cC (SEQ ID No. 3):
5'-TTTAGTTTTTGGACGTCTTCTCCTTT-3'

Target cG (SEQ ID No. 18):
5'-TTTAGTTTTTGGAGGTCTTCTCCTTT-3'

Target cA (SEQ ID No. 19):
5'-TTTAGTTTTTGGAAGTCTTCTCCTTT-3'

Target cT (SEQ ID No. 20):
5'-TTTAGTTTTTGGATGTCTTCTCCTTT-3'
```

The synthetic target sequence "cC" is perfectly complementary to a part of the sequences of the probes. The synthetic target sequences "cG", "cA" and "cT" contain a mispairing relative to the complementary sequence in the probes, indicated by the underlining of the corresponding letter.

The probes are introduced in a solution containing:
A basic kit diluent (bioMérieux B.V., Boxtel, the Netherlands, ref. 70352),
A probe at 0.1 micromolar concentration,
A synthetic target sequence at 1.25 micromolar concentration.

The final volume is 20 μl.

Negative controls are prepared using MilliQ ultrapure water instead of the target sequence. This makes it possible to observe the behavior of the probe alone.

The solutions are heated to 65° C. in the fluorescence reader (EasyQ reader, bioMérieux B.V., Boxtel, the Netherlands) and left to cool for 5 hours. The fluorescence of each solution is measured at 520 nm throughout the cooling. The results are expressed in the form of a graph of temperature (in ° C.) versus fluorescence (in RFU).

Results:

Among the probes tested for the Influenza B model, OPa6 is the one displaying the largest difference of Tm-target between the perfect target (cC) and the targets possessing a mispairing (cG, cA or cT).

TABLE 3

Analytical Tm of the probes of the Influenza B model (first two columns on left) and difference obtained between Tm target with the perfect target (cC) and the targets possessing a mispairing (columns cG and Δ TmcG; cA Δ Tm cA; cT and Δ Tm cT).

|  | Tm stem | Tm target cC (SEQ ID No. 3) | Tm target cG (SEQ ID No. 18) | | Tm target cA (SEQ ID No. 19) | | Tm target cT (SEQ ID No. 20) | |
|---|---|---|---|---|---|---|---|---|
|  |  |  |  | Δ Tm |  | Δ Tm |  | Δ Tm |
| CP InfB (SEQ ID No. 13) | 49.7 | 57.7 | 51.0 | −6.7 | 50.2 | −7.5 | 48.2 | −9.5 |
| Opa 6 (SEQ ID No. 14) | 48.8 | 57.5 | 49.8 | −7.6 | 48.5 | −8.9 | 47.1 | −10.4 |
| Opa 5 (SEQ ID No. 15) | 45.1 | 57.6 | 51.8 | −5.8 | 51.2 | −6.4 | 48.9 | −8.8 |
| Opi 4 (SEQ ID No. 16) | 51.8 | 57.1 | 49.7 | −7.3 | 48.9 | −8.1 | 47.0 | −10.1 |
| Opi 3 (SEQ ID No. 17) | 49.5 | 57.5 | 49.8 | −7.7 | 47.7 | −10.0 | 50.6 | −6.9 |

This table collects together the Tm values measured from the graphs obtained. FIG. 9 shows two examples of these graphs. The difference between Tm-target of the probe with its perfect target and Tm-target of the probe with the targets possessing a mispairing is clearly seen on the graphs and can reach 10° C. for probes OPi4 and OPa6. As Tm-target of the probe with the targets possessing a mispairing is very close to Tm-stem of the probe, the latter closes onto itself before hybridizing with its target.

Conclusions:

The probes according to the invention are specific probes of a given target, and their performance in this area is similar to that of the reference molecular beacon. This is of major interest for the detection of SNPs or Single Nucleotide Polymorphisms corresponding to the variation of a single nucleotide in a given gene.

EXAMPLE 8

Investigation of the Specificity of the Probes According to the Invention on the HIV Model Objectives:

The specificity of a probe is its capacity to recognize only its target, and thus differentiate it from a target that includes for example mispairings or deletions. Molecular beacons are currently the most specific molecular probes since they permit the differentiation of two targets differing by just one nucleotide. The objective of this experiment is to show the level of specificity of the probes according to the invention, in comparison with the molecular beacon probe that contains the same recognition sequence.

Experimental Design:

The probes used are as follows:

```
Molecular beacon HIV-1A (SEQ ID No. 21):
5'(FAM)-CTATCCCATCAATGAGGAAGCTGCAGAATGGGATA
G-3' Da Hoa6 Probe (SEQ ID No. 11):
5'-accctatcc(dT-FAM)ATCAATGAGGAAGCTGCAGAATG
GGATAGG-3' Da Hoa7 (SEQ ID No. 22):
5'-ttaccctatc(dT-FAM)ATCAATGAGGAAGCTGCAGAAT
GGGATAG-3' Da Hoa8 Probe (SEQ ID No. 2):
5'-accctatctc(dT-FAM)CCATCAATGAGGAAGCTGCAGA
ATGGGATAGAG-3' Da Hoi6d Probe (SEQ ID No. 12):
5'-Da-CCATCAATGAGGAAGCTGCAGAATGGGATAGG-3'-
(dT-FAM)-3'-ggtagttact-5'

Hoi7d Probe (SEQ ID No. 23):
5'-Da-CCATCAATGAGGAAGCTGCAGAATGGGATAGG-3'-
(dT-FAM)-3'-ggtagttactc-5'

Hoi8d Probe (SEQ ID No. 6):
5'-Da-CCATCAATGAGGAAGCTGCAGAATGGGATAGAG-3'-
(dT-FAM)-3'-ggtagttactc-5'
```

The segments underlined correspond to the closing sequences of the probes according to the invention and to the sequences of the strands forming the "stem" part of the molecular beacon. The nucleotides written in lower case in the probes according to the invention correspond to nucleotides of the alpha type.

The nucleotides written in lower case and in bold in the probes according to the invention correspond to inverted nucleotides.

The synthetic target sequences used are as follows:

```
Target cH5 (SEQ ID No. 24):
5'-TTTCATTCTGCAGCTTCCTCATTT-3'

Target cGH5 (SEQ ID No. 25):
5'-TTTCATTCTGCAGGTTCCTCATTT-3'

Target cAH5 (SEQ ID No. 26):
5'-TTTCATTCTGCAGATTCCTCATTT-3'

Target cTH5 (SEQ ID No. 27):
5'-TTTCATTCTGCAGTTTCCTCATTT-3'
```

The synthetic target sequence "cH$_5$" is perfectly complementary to a part of the sequences of the probes. The synthetic target sequences "cGH5", "cAH5" and "cTH5" contain a mispairing relative to the complementary sequence in the probes, indicated by the underlining of the corresponding letter.

The probes are introduced in a solution containing:

A basic kit diluent (bioMérieux B.V., Boxtel, the Netherlands, ref. 70352).

A probe at 0.1 micromolar concentration.

A synthetic target sequence at 1.25 micromolar concentration.

The final volume is 20 μl.

Negative controls are prepared using MilliQ ultrapure water instead of the target sequence. This makes it possible to observe the behavior of the probe alone.

The solutions are heated to 65° C. in the fluorescence reader (EasyQ reader, bioMérieux B.V., Boxtel, the Netherlands) and left to cool for 5 hours. The fluorescence of each solution is measured throughout cooling at 520 M. The results are expressed in the form of a graph of temperature versus fluorescence.

Results:

The results are presented in the following table and in FIG. 10.

TABLE 4

Values of Tm-target of the molecular beacon and of the probes according to the
invention of the alpha type and inverted with the perfect target cH5 (first two columns on left)
and difference obtained between Tm-target of the probes with the perfect target (cH5) and
Tm-target of the probes with the targets possessing a mispairing (cAH5, cGH5, cTH5)
(columns Δ Tm cAH5; Δ Tm cGH5; Δ Tm cTH5).

|  | Tm stem cH5 (SEQ ID No. 24) | Tm target cH5 (SEQ ID No. 24) | Δ Tm cGH5 (SEQ ID No. 25) | Δ Tm cAH5 (SEQ ID No. 26) | Δ Tm cTH5 (SEQ ID No. 27) |
|---|---|---|---|---|---|
| HIV-1A (SEQ ID No. 21) | 50.9 | 58.0 | −6.1 | −7.3 | −8.5 |
| HOa6 (SEQ ID No. 11) | 49.0 | 58.3 | −6.4 | −7.5 | −8.8 |
| HOa7 (SEQ ID No. 22) | 44.2 | 58.4 | −6.5 | −7.7 | −8.9 |
| HOa8 (SEQ ID No. 2) | 49.9 | 58.4 | −6.5 | −7.7 | −8.9 |
| Hoi6d (SEQ ID No. 12) | 44.1 | 58.5 | −6.7 | −7.8 | −9.1 |
| Hoi7d (SEQ ID No. 23) | 48.3 | 58.5 | −6.6 | −7.8 | −9.0 |
| Hoi8d (SEQ ID No. 6) | 48.6 | 58.4 | −6.5 | −7.7 | −8.9 |

This table collects together the Tm values measured from the graphs obtained. FIG. 10 shows two examples of these graphs. The difference between Tm with the perfectly complementary target and Tm with the targets that contain a mispairing is clearly seen and can reach 9° C. for probes HOi6d and HOi7d.

Conclusions:

The probes according to the invention are specific probes of a given target, their performance in this area even exceeds that of the reference molecular beacon HIV-1A. This is of major interest for the detection of SNPs or Single Nucleotide Polymorphisms corresponding to the variation of a single nucleotide in a given gene.

EXAMPLE 9

Investigation of the Specific Hybridization of the Probes According to the Invention of the Alpha Type of the Influenza B Model to their Target Sequence Objectives:

The objective of this experiment is to demonstrate that a probe according to the invention hybridizes to a target nucleic acid more specifically than a molecular beacon probe. Generally, when designing a molecular beacon probe, the Tm taken into consideration is that calculated from the recognition sequence, a sequence complementary to the target sequence (calculated Tm). In fact, the sequences of the strands forming the "stem" part of the molecular beacon are considered not to hybridize to the target nucleic acid. Now, the real Tm of the molecular beacon probe can be slightly higher than that calculated, owing to the interactions of the sequences of the strands forming the "stem" part of the molecular beacon with the target sequence. Moreover, the strands forming the "stem" part can hybridize nonspecifically to the sequence of the target, which has the effect of increasing the overall stability of hybridization of the molecular beacon to the target (the real Tm-target is higher than the calculated Tm-target) and of thus decreasing the specificity of this hybridization.

Experimental Design:

The probes used are as follows:

```
Opa6d Probe (SEQ ID No. 1):
5'-gaccgtctg(dT-FAM)GGAGAAGACGTCCAAAAACT
GGCAGAC-3' Da Molecular beacon CpinfB (SEQ ID No. 13):
5'-(FAM)-CGATCGGGAGAAGACGTCCAAAAACTCGATC
G-3'Da
```

The segments underlined correspond to the closing sequences of the probes according to the invention or to the strands of the "stem" part of the molecular beacon.

The nucleotides written in lower case in the probes correspond to nucleotides of the alpha type.

The synthetic target sequences used are as follows:

```
Target Bioa2I (SEQ ID No. 28):
5'-TTTAGTTTTTGGACGTCTTCTCCTTTTCCAATT-3'
Target 6Ba2I (SEQ ID No. 29):
5'-TTTAGTTTTTGGACGTCTTCTCCCGATCGAATT-3'
Target 10Pa2I (SEQ ID No. 30):
5'-TTTAGTTTTTGGACGTCTTCTCCACAGACGGTC-3'
Target 6Pa2I (SEQ ID No. 31):
5'-TTTAGTTTTTGGACGTCTTCTCCACAGACAATT-3'
Target 1Ba2I (SEQ ID No. 32):
5'-TTTAGTTTTTGGACGTCTTCTCCCTTTCCAATT-3'
Target 1Pa2I (SEQ ID No. 33):
5'-TTTAGTTTTTGGACGTCTTCTCCATTTCCAATT-3'
Target 2Ba2I (SEQ ID No. 34):
5'-TTTAGTTTTTGGACGTCTTCTCCCGTTCCAATT-3'
Target 2Ba2I (SEQ ID No. 35):
5'-TTTAGTTTTTGGACGTCTTCTCCACTTCCAATT-3'
```

The sequence underlined with a dotted line corresponds to the part that can hybridize to the recognition sequence either of the molecular beacon CpinfB (SEQ ID No. 13), or of the probe according to the invention Opa6d (SEQ ID No. 1).

The sequence Bioa2I (SEQ ID No. 28) corresponds to a fragment of the biological target sequence of the influenza B virus.

The target sequence 6Ba2I (SEQ ID No. 29) contains, relative to the target sequence Bioa2I (SEQ ID No. 28), six nucleotides at 3' of the sequence underlined with a dotted line. These six nucleotides, with double underlining, are complementary to the sequence of one of the strands of the "stem" part of the molecular beacon CpinfB (SEQ ID No. 13).

The target sequence 10 Pa2I (SEQ ID 30) contains, relative to the target sequence Bioa2I (SEQ ID No. 28), ten nucleotides at 3' of the sequence highlighted with dotted lines. These ten nucleotides, with double underlining, are complementary to one of the closing sequences of the probe according to the invention Opa6d (SEQ ID No. 1).

The target sequence 6 Pa2I (SEQ ID No. 31) contains, relative to the target sequence Bioa2I (SEQ ID No. 28), six nucleotides at 3' of the sequence underlined with a dotted line. These six nucleotides, with double underlining, are complementary to one of the closing sequences of the probe according to the invention Opa6d (SEQ ID No. 1).

The target sequence 1Ba2I (SEQ ID No. 32) contains, relative to sequence Bioa2I (SEQ ID No. 28), a nucleotide at 3' of the sequence underlined with a dotted line. This nucleotide, with double underlining, is complementary to a nucleotide of the sequence of one of the strands of the "stem" part of the molecular beacon CpinfB (SEQ ID No. 13).

The target sequence 1Pa2I (SEQ ID No. 33) contains, relative to sequence Bioa2I (SEQ ID No. 28), a nucleotide at 3' of the sequence underlined with a dotted line. This nucleotide, with double underlining, is complementary to one of the closing sequences of the probe according to the invention Opa6d (SEQ ID No. 1).

The target sequence 2Ba2I (SEQ ID No. 34) contains, relative to sequence Bioa2I (SEQ ID No. 28), two nucleotides at 3' of the sequence highlighted with dotted lines. These two nucleotides, with double underlining, are complementary to the sequence of one of the strands of the "stem" part of the molecular beacon CpinfB (SEQ ID No. 13).

The target sequence 2Pa2I (SEQ ID No. 35) contains, relative to the target sequence Bioa2I (SEQ ID No. 28), two nucleotides at 3' of the sequence underlined with a dotted line. These two nucleotides, with double underlining, are complementary to one of the closing sequences of the probe according to the invention Opa6d (SEQ ID No. 1).

The probes are introduced in a solution containing:
Basic kit diluent (bioMérieux B.V, Boxtel, the Netherlands, ref. 70352),
Probe at 0.1 micromolar concentration,
Synthetic target sequence at 1.25 micromolar concentration.
The final volume is 20 μl.
Negative controls are made with water in place of the target sequence. This makes it possible to observe the behavior of the probe alone.

The solutions are heated to 68° C. in the fluorescence reader (EasyQ reader, bioMérieux B.V, Boxtel, the Netherlands) and left to cool for 5 hours. The fluorescence of each solution is measured at 520 nm throughout the cooling. The thermal stability of the probe/target double helix is given by the value of "Tm-target" that corresponds to the turning point of the curve fluorescence=f(temperature). Tm-target is calculated as the minimum of the first derivative of this curve.
Results:

The results are presented in Table 5 and FIG. 7. Table 5 collects together the values of Tm-target (in ° C.) obtained with the probes and targets described in this example. The increase in Tm-target relative to a reference Tm-target indicates the development of additional interactions between the target and its probe. In this example, the reference Tm-target values correspond to the Tm-target values measured between the molecular beacon CpinfB (SEQ ID No. 13) and the target Bioa2I (SEQ ID No. 28) and to that measured between the probe according to the invention Opa6d (SEQ ID No. 1) and the target Bio2aI (SEQ ID No. 28). They are equal to 57.3° C. and 56.4° C. respectively.

TABLE 5

Presentation of the values of Tm-target obtained with the various probes.

| | | Probes | |
| --- | --- | --- | --- |
| | | CPInfB (SEQ ID No. 13) | Opa6d (SEQ ID No. 1) |
| Target sequences | Bioa2I (SEQ ID No. 28) | 57.3 | 56.4 |
| | 6Ba2I (SEQ ID No. 29) | 65 | 57.8 |
| | 10Pa2I (SEQ ID No. 30) | 57.2 | 57.2 |
| | 6Pa2I (SEQ ID No. 31) | 58.6 | 58.4 |
| | 1Ba2I (SEQ ID No. 32) | 58.8 | 56.5 |
| | 1Pa2I (SEQ ID No. 33) | 57 | 56.6 |
| | 2Ba2I (SEQ ID No. 34) | 60.6 | 56.5 |
| | 2Pa2I (SEQ ID No. 35) | 57.3 | 57.3 |

The molecular beacon probe CpinfB (SEQ ID No. 13), when it is in solution in the presence of various synthetic target sequences, hybridizes to them and produces a measurable fluorescence signal. When the synthetic target contains nucleotides complementary to the sequence of one of the strands of the "stem" part of the molecular beacon CPinfB, an increase in Tm-target of the molecular beacon probe is observed. This increase is proportional to the number of nucleotides complementary to the sequence of one of the strands of the stem part of the molecular beacon, and indicates that there is base pairing between the nucleotides of the sequence of one of the strands of the "stem" part of the CPinfB probe and the complementary nucleotides that are adjacent to the sequence hybridized to the target.

When the probe according to the invention Opa6d (SEQ ID No. 1) (probe of the alpha type) is in solution in the presence of various synthetic target sequences, it hybridizes to them and produces a measurable fluorescence signal. When the synthetic target contains nucleotides complementary to one of the closing sequences of the probe according to the invention Opa6d, it is observed that the values of Tm-target of the probe according to the invention remain stable, regardless of the number of said complementary nucleotides. This indicates that there is no base pairing between the nucleotides of one of the closing sequences of the probe according to the invention and the complementary nucleotides that are adjacent to the sequence hybridized to the target.

Conclusion:

The probe according to the invention Opa6d is more specific than the molecular beacon probe CPinfB as there are no additional interactions between the nucleotides of one of the closing sequences of the probe and the sequence of the target even if these nucleotides are complementary to each other. The only part of the probe according to the invention that hybridizes to the target nucleic acid corresponding to the molecular recognition sequence of the Opa6d probe. The design of this probe greatly reduces the possibilities for non-specific hybridization of the probe according to the invention to sequences close to the sequence of the target.

EXAMPLE 10

Investigation of Hybridization of the Specific Probes According to the Invention of the Alpha Type at 5' of the HIV Model to their Target Sequence Objectives:

The objective in this example is the same as that already described in example 9 for a different target model.

Experimental Design:

The probes used are as follows:

```
HOa8 Probe (SEQ ID No. 2):
5'-accctatctc(dT-FAM)CCATCAATGAGGAAGCTGCAGA
ATGGGATAGAG-3'Da Molecular beacon HIV-1A (SEQ ID No. 21):
5'-(FAM)CTATCCCATCAATGAGGAAGCTGCAGAATGGGATA
G-3'Da
```

The segments underlined correspond to the closing sequences of the probes according to the invention or to the strands of the "stem" part of the molecular beacon.

The nucleotides written in lower case in the probes correspond to nucleotides of the alpha type.

The synthetic target sequences used are as follows:

```
Target BioH (SEQ ID No. 36):
TTTCATTCTGCAGCTTCCTCATTGATGGTCTCTTTTAAC
Target 5BH (SEQ ID No. 37):
TTTCATTCTGCAGCTTCCTCATTGATGGGATAGTTTAAC
Target 11PH (SEQ ID No. 38):
TTTCATTCTGCAGCTTCCTCATTGATGGAGAGATAGGGT
Target 5PH (SEQ ID No. 39):
TTTCATTCTGCAGCTTCCTCATTGATGGAGAGATTTAAC
Target 1BH (SEQ ID No. 40):
TTTCATTCTGCAGCTTCCTCATTGATGGGCTCTTTTAAC
Target 1PH (SEQ ID No. 41):
TTTCATTCTGCAGCTTCCTCATTGATGGACTCTTTTAAC
Target 2BH (SEQ ID No. 42):
TTTCATTCTGCAGCTTCCTCATTGATGGGATCTTTTAAC
Target 2PH (SEQ ID No. 43):
TTTCATTCTGCAGCTTCCTCATTGATGGAGTCTTTTAAC
```

The sequence underlined with a dotted line corresponds to the part that can hybridize to the recognition sequence either of the molecular beacon HIV-1A (SEQ ID No. 21) or of the probe according to the invention HOa8 (SEQ ID No. 2).

The target sequence BioH (SEQ ID No. 36) corresponds to a fragment of the biological target sequence of the HIV virus. It can contain a nucleotide complementary to a closing sequence of the probes according to the invention or to one of the sequences of the strands of the "stem" part of the molecular beacon.

The target sequence 5BH (SEQ ID No. 37) contains, relative to the target sequence BioH (SEQ ID No, 36), five nucleotides at 3' of the sequence underlined with a dotted line. These five nucleotides, with double underlining, are complementary to the sequence of one of the strands of the "stem" part of the molecular beacon HIV-1A (SEQ ID No. 21).

The target sequence 11PH (SEQ ID No. 38) contains, relative to the target sequence BioH (SEQ ID No. 36), eleven nucleotides at 3' of the sequence highlighted with dotted lines. These eleven nucleotides, with double underlining, are complementary to one of the closing sequences of the probe according to the invention HOa8 (SEQ ID No. 2).

The target sequence 5PH (SEQ ID No. 39) contains, relative to the target sequence BioH (SEQ ID No. 36), five nucleotides at 3' of the sequence underlined with a dotted line. These five nucleotides, with double underlining, are complementary to one of the closing sequences of the probe according to the invention HOa8 (SEQ ID No. 2).

The target sequence 1BH (SEQ ID No. 40) contains, relative to the target sequence BioH (SEQ ID No. 36), a nucleotide at 3' of the sequence underlined with a dotted line. This nucleotide, with double underlining, is complementary to the sequence of one of the strands of the "stem" part of the molecular beacon HIV-1A (SEQ ID No. 21).

The target sequence 1PH (SEQ ID No. 41) contains, relative to the target sequence BioH (SEQ ID No. 36), a nucleotide at 3' of the sequence underlined with a dotted line. This nucleotide, with double underlining, is complementary to one of the closing sequences of the probe according to the invention HOa8 (SEQ ID No. 2).

The target sequence 2BH (SEQ ID No. 42) contains, relative to the target sequence BioH (SEQ ID No. 36), two nucleotides at 3' of the sequence underlined with a dotted line. These nucleotides, with double underlining, are complementary to the sequence of one of the strands of the "stem" part of the molecular beacon HIV-1A (SEQ ID No. 21).

The target sequence 2PH (SEQ ID No. 43) contains, relative to the target sequence BioH (SEQ ID No. 36), two nucleotides at 3' of the sequence underlined with a dotted line. These two nucleotides, with double underlining, are complementary to one of the closing sequences of the probe according to the invention HOa8 (SEQ ID No. 2).

The probes are introduced in a solution containing:

Basic kit diluent (bioMérieux B.V., Boxtel, the Netherlands, ref. 70352),

Probe at 0.1 micromolar concentration,

Synthetic target sequence at 1.25 micromolar concentration.

The final volume is 20 µl.

Negative controls are made with MilliQ ultrapure water in place of the target sequence. This makes it possible to observe the behavior of the probe alone.

The solutions are heated to 68° C. in the fluorescence reader (EasyQ reader, bioMérieux B.V., Boxtel, the Netherlands) and left to cool for 5 hours. The fluorescence of each solution is measured at 520 nm throughout the cooling. The thermal stability of the probe/target double helix is given by the value of "Tm-target" that corresponds to the turning point of the curve fluorescence=f(temperature). Tm-target is calculated as the minimum of the first derivative of this curve.

Results:

The results are presented in Table 6 and in FIG. 8. Table 6, given below, collects together the values of Tm-target (in ° C.) obtained with the probes and targets described in this example. The increase in Tm-target relative to a reference Tm-target indicates the development of additional interactions between the target and its probe. In this example, the reference Tm-target values correspond to the Tm-target values measured between the molecular beacon HIV-1A (SEQ ID No. 21) and the target BioH (SEQ ID No. 36) and that measured between the probe according to the invention Hoa8 (SEQ ID No. 2) and the target BioH (SEQ ID No. 36). They are equal to 60.6° C. and 60.2° C. respectively.

TABLE 6

Presentation of the values of Tm-target obtained with the various probes.

|  |  | Probes | |
|---|---|---|---|
|  |  | HIV-1A (SEQ ID No. 21) | HOa8 (SEQ ID No. 2) |
| Target sequences | BioH (SEQ ID No. 36) | 60.6 | 60.2 |
|  | 5BH (SEQ ID No. 37) | 68* | 60.8 |
|  | 11PH (SEQ ID No. 38) | 60.8 | 60.3 |
|  | 5PH (SEQ ID No. 39) | 61.5 | 60.8 |
|  | 1BH (SEQ ID No. 40) | 61.4 | NA |
|  | 1PH (SEQ ID No. 41) | 61.5 | 60.9 |
|  | 2BH (SEQ ID No. 42) | 63 | 61.3 |
|  | 2PH (SEQ ID No. 43) | 61.6 | 61.3 |

*The value of Tm between the molecular beacon HIV-1A (SEQ ID No. 21) and the complementary target 5BH (SEQ ID No. 37) was higher than the maximum value measurable of 68° C. For the purposes of the experiment, we have shown the maximum possible value that can be measured.
NA: Not Applicable.
The value of Tm between the probe according to the invention HOa8 (SEQ ID No. 2) and the complementary target 1BH (SEQ ID No. 40) could not be measured as the profile does not correspond to the standard measurable with our method. This value was determined from an empirical reading of the graph and is 60° C.

The molecular beacon probe HIV-1A (SEQ ID No. 21), when it is in solution in the presence of various synthetic target sequences, hybridizes to them and produces a measurable fluorescence signal. When the synthetic target contains nucleotides complementary to the sequence of one of the strands of the "stem" part of the molecular beacon HIV-1A, an increase in Tm-target of the molecular beacon probe is observed. This increase is proportional to the number of nucleotides complementary to the sequence of one of the strands of the "stem" part, and indicates that there is base pairing between these nucleotides and the complementary nucleotides that are adjacent in the sequence hybridized to the target.

When the probe according to the invention HOa8 (SEQ ID No. 2) (of the alpha type) is in solution in the presence of various synthetic target sequences, it hybridizes to these sequences and produces a measurable fluorescence signal. When the synthetic target contains nucleotides complementary to one of the closing sequences of the HOa8 probe, Tm-target of the probe according to the invention of the alpha type remains stable, indicating that there is no base pairing between the nucleotides of one of the closing sequences of the probe according to the invention and the complementary nucleotides that are adjacent in the sequence hybridized to the target.

Conclusion:

The probe according to the invention HOa8 is more specific than the molecular beacon probe HIV-1A as there are no additional interactions between the nucleotides of one of the closing sequences of the probe and the sequence of the target even if these nucleotides are complementary to each other. The only part of the probe according to the invention that hybridizes to the target nucleic acid corresponding to the molecular recognition sequence of the HOa8 probe. The design of this probe greatly reduces the possibilities for non-specific hybridization of the probe according to the invention to sequences close to the sequence of the target.

EXAMPLE 11

Investigation of the Specific Hybridization of the Probes According to the Invention of the Inverted Type at 3' of the Influenza B Model to Their Target Sequence Objectives:

The objective in this example is the same as that described in example 9 but with a different design of the probe according to the invention.

Experimental Design:

The probes used are as follows:

```
Opi6d Probe (SEQ ID No. 5):
5'-Da-GGAGAAGACGTCCAAAAACTGGCAGA-3'(dT-FAM)
3'-cctcttctg-5'

Molecular beacon CP2infB (SEQ ID No. 13):
5'-CGATCGGGAGAAGACGTCCAAAAACTGGCAGACGATC
G-3'Da
```

The segments underlined correspond to the closing sequences of the probes according to the invention or to the strands of the "stem" part of the molecular beacon.

The nucleotides written in lower case and in bold in the probes correspond to nucleotides of the inverted type.

The synthetic target sequences used are as follows:

```
Target BioiI (SEQ ID No. 44):
TTGCAGCTCTTCTGCCAGTTTTTGGACGTCTTCTCCTTT

Target 6BiI (SEQ ID No. 45):
TTGCCGATCGTCTGCCAGTTTTTGGACGTCTTCTCCTTT

Target 10PiI (SEQ ID No. 46):
CAGAAGAGGATCTGCCAGTTTTTGGACGTCTTCTCCTTT

Target 6PiI (SEQ ID No. 47):
TTGCAGAGGATCTGCCAGTTTTTGGACGTCTTCTCCTTT

Target 1BiI (SEQ ID No. 48):
TTGCAGCTCGTCTGCCAGTTTTTGGACGTCTTCTCCTTT

Target 1PiI (SEQ ID No. 49):
TTGCAGCTCATCTGCCAGTTTTTGGACGTCTTCTCCTTT
```

The sequence underlined with a dotted line corresponds to the part that can hybridize to the recognition sequence either of the molecular beacon CP2infB (SEQ ID No. 13) or of the probe according to the invention HOa8 (SEQ ID No. 5).

The target sequence BioiI (SEQ ID No, 44) corresponds to a fragment of the biological target sequence of the influenza B virus. It can contain a nucleotide complementary to a closing sequence of the probes according to the invention or to a sequence of the strands of the "stem" part of the molecular beacon.

The target sequence 6BiI (SEQ ID No. 45) contains, relative to the target sequence BioiI (SEQ ID No. 44), six nucleotides at 5' of the sequence underlined with a dotted line. These six nucleotides, with double underlining, are complementary to the sequence of one of the strands of the "stem" part of the molecular beacon CP2infB (SEQ ID No. 13).

The target sequence 10PiI (SEQ ID No. 46) contains, relative to the target sequence BioiI (SEQ ID No. 44), ten nucleotides at 5' of the sequence underlined with a dotted line. These ten nucleotides, with double underlining, are complementary to one of the closing sequences of the probe according to the invention Opi6d (SEQ ID No. 5).

The target sequence 6PiI (SEQ ID No, 47) contains, relative to the target sequence BioiI (SEQ ID No. 44), six nucleotides at 5' of the sequence underlined with a dotted line.

These six nucleotides, with double underlining, are complementary to the sequence of one of the closing sequences of the probe according to the invention Opi6d (SEQ ID No. 5).

The target sequence 1BiI (SEQ ID No. 48) contains, relative to the target sequence BioiI (SEQ ID No. 44), a nucleotide at 5' of the sequence underlined with a dotted line. This nucleotide, with double underlining, is complementary to the sequence of one of the strands of the "stem" part of the molecular beacon CP2infB (SEQ ID No. 13).

The target sequence 1PiI (SEQ ID No. 49) contains, relative to the target sequence BioiI (SEQ ID No. 44), a nucleotide at 5' of the sequence underlined with a dotted line. This nucleotide, with double underlining, is complementary to one of the closing sequences of the probe according to the invention Opi6d (SEQ ID No. 5).

The probes are introduced in a solution containing:
Basic kit diluent (bioMérieux B.V., Boxtel, the Netherlands, ref. 70352),
Probe at 0.1 micromolar concentration,
Synthetic target sequence at 1.25 micromolar concentration.
The final volume is 20 µl.

Negative controls are made with ultrapure water of the MilliQ type in place of the target sequence. This makes it possible to observe the behavior of the probe alone.

The solutions are heated to 68° C. in the fluorescence reader (EasyQ reader, bioMérieux B.V, Boxtel, the Netherlands) and left to cool for 5 hours. The fluorescence of each solution is measured at 520 nm throughout the cooling. The thermal stability of the probe/target double helix is given by the value of "Tm-target" that corresponds to the turning point of the curve. Tm-target is calculated as the minimum of the first derivative of the curve.

Results:

The results are presented in Table 7 and FIG. 9. Table 7 collects together the values of Tm-target (in ° C.) obtained with the probes and targets described in this example. The increase in Tm-target relative to a reference Tm-target indicates the development of additional interactions between the target and its probe. In this example, the reference Tm-target values correspond to the Tm-target values measured between the molecular beacon CP2infB (SEQ ID No. 13) and the target BioiI (SEQ ID No. 44) and to that measured between the probe according to the invention Opi6d (SEQ ID No. 5) and the target BioiI (SEQ ID No. 44). They are equal to 62° C. and 62.9° C. respectively.

TABLE 7

Presentation of the values of Tm-target obtained with the various probes.

| | | Probes | |
| --- | --- | --- | --- |
| | | CP2infB (SEQ ID No. 13) | OPi6d (SEQ ID No. 5) |
| Target sequences | BioiI (SEQ ID No. 44) | 62 | 62.9 |
| | 6BiI (SEQ ID No. 45) | 68* | 64.5 |
| | 10PiI (SEQ ID No. 46) | 62.8 | 64.4 |
| | 6PiI (SEQ ID No. 47) | 62.4 | 63.4 |
| | 1BiI (SEQ ID No. 48) | 64.7 | 63.9 |
| | 1PiI (SEQ ID No. 49) | 61.9 | 62.7 |

*The value of Tm between the molecular beacon CP2infB (SEQ ID No. 13) and the complementary target 6BiI (SEQ ID No. 45) was higher than the maximum value measurable of 68° C. For the purposes of the experiment, we have shown the maximum possible value that can be measured.

The molecular beacon probe CP2infB (SEQ ID No. 13), when it is in solution in the presence of various synthetic target sequences, hybridizes to these synthetic target sequences and produces a measurable fluorescence signal. When the synthetic target contains nucleotides complementary to the sequence of one of the strands of the "stem" part of the molecular beacon probe CP2infB (SEQ ID No. 13), we observe a proportional increase of the value of Tm-target of the molecular beacon probe relative to the number of nucleotides complementary to the sequence of one of the strands of the "stem" part. This indicates that there is base pairing between the nucleotides of one of the strands of the "stem" part of the probe CP2infB (SEQ ID No. 13) and the complementary nucleotides that are adjacent in the sequence of the target.

The probe according to the invention Opi6d (of the inverted type) (SEQ ID No. 5), when it is in solution in the presence of various synthetic target sequences, hybridizes to these synthetic target sequences and produces a measurable fluorescence signal. When the synthetic target contains complementary nucleotides of one of the closing sequences of the probe according to the invention Opi6d (SEQ ID No. 5), Tm-target of the probe according to the invention of the inverted type remains stable, indicating that there is no base pairing between the nucleotides of one of the closing sequences of the probe and the complementary nucleotides that are adjacent in the sequence of the target.

Conclusion

The probe according to the invention Opi6d is more specific than the molecular beacon probe CPinfB as there are no additional interactions between the nucleotides of one of the closing sequences of the probe and the sequence of the target even if these nucleotides are complementary to each other. The only part of the probe according to the invention that hybridizes to the target nucleic acid corresponding to the molecular recognition sequence of the probe Opi6d. The design of this probe greatly reduces the possibilities for non-specific hybridization of the probe according to the invention to sequences close to the sequence of the target.

EXAMPLE 12

Investigation of Hybridization of the Probes According to the Invention of the Inverted Type at 5' of the Hiv Model to their Target Sequence Objectives:

The objective in this example is the same as that described in example 9 but with a different design of the probe according to the invention and a different model of the target.

Experimental Design:

The probes used are as follows:

HOi8 Probe (SEQ ID No. 50):
3'-accctatctc-5'-5'-(dT-FAM)CCATCAATGAGGAAGC
TGCAGAATGGGATAGAG-3'Da HIV-1A reference molecular beacon (SEQ ID No. 21):
5'-(FAM)-CTATCCCATCAATGAGGAAGCTGCAGAATGGGATA
G-3' Da The segments underlined correspond to the closing sequences of the probes according to the invention or to the strands of the "stem" part of the molecular beacon.

The nucleotides written in lower case and in bold in the probes correspond to nucleotides of the inverted type.

The synthetic target sequences used are as follows:

```
Target BioH (SEQ ID No. 36):
5'-TTTCATTCTGCAGCTTCCTCATTGATGGTCTCTTTTAAC-3'
Target 5BH (SEQ ID No. 37):
5'-TTTCATTCTGCAGCTTCCTCATTGATGGGATAGTTAAC-3'
Target 11PH (SEQ ID No. 38):
5'-TTTCATTCTGCAGCTTCCTCATTGATGGAGAGATAGGGT-3'
Target 5PH (SEQ ID No. 39):
5'-TTTCATTCTGCAGCTTCCTCATTGATGGAGAGATTAAC-3'
Target 1BH (SEQ ID No. 40):
5'-TTTCATTCTGCAGCTTCCTCATTGATGGGCTCTTTTAAC-3'
Target 1PH (SEQ ID No. 41):
5'-TTTCATTCTGCAGCTTCCTCATTGATGGACTCTTTTAAC-3'
Target 2BH (SEQ ID No. 42):
5'-TTTCATTCTGCAGCTTCCTCATTGATGGGATCTTTTAAC-3'
Target 2PH (SEQ ID No. 43):
5'-TTTCATTCTGCAGCTTCCTCATTGATGGAGTCTTTTAAC-3'
```

The sequence underlined with a dotted line corresponds to the part that can hybridize to the recognition sequence either of the molecular beacon HIV-1A (SEQ ID No. 21) or of the probe according to the invention HOi8 (SEQ ID No. 50).

The target sequence BioH (SEQ ID No. 36) corresponds to a fragment of the biological target sequence of the HIV virus. It can contain a nucleotide complementary to a closing sequence of the probes according to the invention or to a sequence of the strands of the "stem" part of the molecular beacon.

The target sequence 5BH (SEQ ID No. 37) contains, relative to the target sequence BioH (SEQ ID No. 36), five nucleotides at 3' of the sequence underlined with a dotted line. These five nucleotides, with double underlining, are complementary to the sequence of one of the strands of the "stem" part of the molecular beacon HIV-1A (SEQ ID No. 21).

The target sequence 11PH (SEQ ID No. 38) contains, relative to the target sequence BioH (SEQ ID No. 36), eleven nucleotides at 3' of the sequence underlined with a dotted line. These eleven nucleotides, with double underlining, are complementary to one of the closing sequences of the probe according to the invention HOi8 (SEQ ID No. 50).

The target sequence 5PH (SEQ ID No. 39) contains, relative to the target sequence BioH (SEQ ID No. 36), five nucleotides at 3' of the sequence underlined with a dotted line. These five nucleotides, with double underlining, are complementary to one of the closing sequences of the probe according to the invention HOi8 (SEQ ID No. 50).

The target sequence 1BH (SEQ ID No. 40) contains, relative to the target sequence BioH (SEQ ID No. 36), a nucleotide at 3' of the sequence underlined with a dotted line. This nucleotide, with double underlining, is complementary to the sequence of one of the strands of the "stem" part of the molecular beacon HIV-1A (SEQ ID No. 21).

The target sequence 1PH (SEQ ID No. 41) contains, relative to the target sequence BioH (SEQ ID No. 36), a nucleotide at 3' of the sequence underlined with a dotted line. This nucleotide, with double underlining, is complementary to one of the closing sequences of the probe according to the invention HOi8 (SEQ ID No. 50).

The target sequence 2BH (SEQ ID No. 42) contains, relative to the target sequence BioH (SEQ ID No. 36), two nucleotides at 3' of the sequence underlined with a dotted line. These two nucleotides, with double underlining, are complementary to the sequence of one of the strands of the "stem" part of the molecular beacon HIV-1A (SEQ ID No. 21).

The target sequence 2PH (SEQ ID No. 43) contains, relative to the target sequence BioH (SEQ ID No. 36), two nucleotides at 3' of the sequence underlined with a dotted line. These two nucleotides, with double underlining, are complementary to one of the closing sequences of the probe according to the invention HOi8 (SEQ ID No. 50).

The probes are introduced in a solution containing:
Basic kit diluent (bioMérieux B.V., Boxtel, the Netherlands, ref. 70352),
Probe at 0.1 micromolar concentration,
Synthetic target sequence at 1.25 micromolar concentration.
The final volume is 20

Negative controls are made with ultrapure water of the MilliQ type in place of the target sequence. This makes it possible to observe the behavior of the probe alone. The solutions are heated to 68° C. in the fluorescence reader (EasyQ reader, bioMérieux B.V., Boxtel, the Netherlands) and left to cool for 5 hours. The fluorescence of each solution is measured at 520 nm throughout the cooling. The thermal stability of the probe/target double helix is given by the value of "Tm-target" that corresponds to the turning point of the curve. Tm-target is calculated as the minimum of the first derivative of the curve.

Results:

The results are presented in Table 8 and FIG. 10. Table 8 collects together the values of Tm-target (in ° C.) obtained with the probes and targets described in this example. The increase in Tm-target relative to a reference Tm-target indicates the development of additional interactions between the target and its probe. In this example, the reference Tm-target values correspond to the Tm-target values measured between the molecular beacon HIV-1A (SEQ ID No. 21) and the target BioH (SEQ ID No. 36) and to that measured between the probe according to HOi8 (SEQ ID No, 50) and the target BioH (SEQ ID No, 36). They are equal to 60.6° C. and 61.1° C. respectively.

TABLE 8

Presentation of the values of Tm-target obtained with the various probes.

| | | Probes | |
| --- | --- | --- | --- |
| | | HIV-1A (SEQ ID No. 21) | HOi8 (SEQ ID No. 50) |
| Target sequences | BioH (SEQ ID No. 36) | 60.6 | 61.1 |
| | 5BH (SEQ ID No. 37) | 68* | 60.7 |
| | 11PH (SEQ ID No. 38) | 60.8 | 61.3 |
| | 5PH (SEQ ID No. 39) | 61.5 | 62.2 |
| | 1BH (SEQ ID No. 40) | 61.4 | 60.6 |
| | 1PH (SEQ ID No. 41) | 61.5 | 60.9 |
| | 2BH (SEQ ID No. 42) | 63 | 62.3 |
| | 2PH (SEQ ID No. 43) | 61.6 | 62.3 |

*The value of Tm between the molecular beacon HIV-1A and the complementary target 5BH was higher than the maximum value measurable of 68° C. For the purposes of the experiment, we have shown the maximum possible value that can be measured.

The molecular beacon probe HIV-1A (SEQ ID No. 21), when it is in solution in the presence of various synthetic target sequences, hybridizes to these synthetic target sequences and produces a measurable fluorescence signal. When the synthetic target contains nucleotides complementary to the sequence of one of the strands of the "stem" part of the molecular beacon HIV-1A (SEQ ID No. 21), it is observed that Tm-target of the molecular beacon probe increases proportionally relative to the number of nucleotides complementary to the sequence of one of the strands of the "stem" part. This indicates that there is base pairing between the nucleotides of the sequence of one of the strands of the "stem" part of the probe HIV-1A (SEQ ID No. 21) and the complementary nucleotides that are adjacent in the sequence of the target.

The probe according to the invention HOi8 (of the inverted type) (SEQ ID No. 50), when it is in solution in the presence of various synthetic target sequences, hybridizes to these synthetic target sequences and produces a measurable fluorescence signal. When the synthetic target contains nucleotides complementary to one of the closing sequences of the probe according to the invention HOi8 (SEQ ID No. 50), Tm-target of the probe according to the invention of the inverted type remains stable, indicating that there is no base pairing between the nucleotides of one of the closing sequences of the probe according to the invention and the complementary nucleotides that are adjacent in the sequence of the target.

Conclusion:

The probe according to the invention Hoi8 is more specific than the molecular beacon probe HIV-1A as there are no additional interactions between the nucleotides of one of the closing sequences of the probe and the sequence of the target even if these nucleotides are complementary to each other. The only part of the probe according to the invention that hybridizes to the target nucleic acid corresponding to the molecular recognition sequence of the probe Hoi8. The design of this probe greatly reduces the possibilities for nonspecific hybridization of the probe according to the invention to sequences close to the sequence of the target.

General Conclusion:

These examples demonstrate that regardless of the design of the probe according to the invention, the latter displays a specificity of hybridization greater than that of a molecular beacon probe. The nature of the nucleotides (alpha nucleotide or inverted nucleotide) as well as their position relative to the second fragment of the probe according to the invention (position at 3' or position at 5') does not affect the quality of the design or the specificity of hybridization of the probe according to the invention for its target nucleic acid.

EXAMPLE 13

Investigation of the Decrease of the Nonspecific Signal of Enzymatic Origin by Using the Probes According to the Invention Objectives:

The objective of this example is to investigate the sensitivity of the probes according to the invention relative to undesirable phenomena of premature opening of said probes.

Experimental Design:

The probes are incubated together with the T7 RNA polymerase enzyme used in NASBA in the reaction mixture, whose composition is described below, for four hours at 41° C., in the fluorescence reader (EasyQ reader, bioMérieux B.V., Boxtel, the Netherlands). The composition of the reaction mixture is:

- 10 µL of "reagent mix", prepared following the supplier's instructions from a NucliSens EQ Basic Kit reagent sphere (bioMérieux B.V., Boxtel, NL, art. No. 60085110) diluted in 64 microliters of Basic Kit reagent sphere diluent (bioMérieux B.V., Boxtel, NL, Art. No. 70352),
- 3.76 microliters of sorbitol (bioMérieux B.V., Boxtel, NL, Art, No. 60085192),
- 0.2 microliters of enzyme T7 RNA Polymerase at a concentration of 80 units per microliter (bioMérieux B.V., Boxtel, NL, Art. No. 72236),
- 2 microliters of probe at an initial concentration of 2 micromolar.

Sufficient quantity of "enzyme mix solution" for a final volume of 20 microliters.

A reference reaction mixture is prepared, containing all the components except the enzyme, which is replaced with an equivalent volume of "enzyme mix solution".

The "enzyme mix solution" is prepared by mixing several other solutions, as follows:

80 microliters of RT storage buffer (bioMérieux B.V., Boxtel, NL, Art. No. 60085341), 114 microliters of T7 storage buffer (bioMérieux BY., Boxtel, NL, Art. No. 60085337), 20 microliters of RH storage buffer (bioMérieux B.V., Boxtel, NL, Art. No. 60085339), 411 microliters of Premix solution (bioMérieux B.V., Boxtel, NL, Art. No. 60085335), 625 microliters of ultrapure water of the MilliQ type.

The fluorescence signal is recorded for four hours at 41° C., at the emission wavelength of fluorescein.

The probes used are as follows:

```
Opi6d Probe (SEQ ID No. 5):
5'-Da-GGAGAAGACGTCCAAAAACTGGCAGA-3'(dT-FAM)
3'-cctcttctg-5'

Opa6d Probe (SEQ ID No. 1):
5'-gaccgtag(dT-FAM)GGAGAAGACGTCCAAAAACTGGCAGA
C-3' Da HOi8 Probe (SEQ ID No. 50):
3'-accctatctc-5'-5'-(dT-FAM)CCATCAATGAGGAAGCTG
CAGAATGGGATAGAG-3' Da HOa8 Probe (SEQ ID No. 2):
5'-accctatctc(dT-FAM)CCATCAATGAGGAAGCTGCAGAATG
GGATAGAG-3' Da Molecular beacon HIV-1A (SEQ ID No. 21):
5'-(FAM)-CTATCCCATCAATGAGGAAGCTGCAGAATGGGATA
G-3' Da Molecular beacon CpinfB (SEQ ID No. 13):
5'-(FAM)-CGATCGGGAGAAGACGTCCAAAAACTCGATCG-3'Da
```

The nucleotide sequences underlined correspond to the closing sequences of the probes according to the invention or to the sequences of the strands forming the "stem" part of the molecular beacon.

The nucleotides written in lower case in the probes correspond to nucleotides of the alpha type. The nucleotides written in lower case and in bold in the probes correspond to inverted nucleotides.

Results:

The fluorescence emission is measured during incubation of the various probes in the presence (FIG. 11a) or in the absence (FIG. 11b) of T7 RNA polymerase enzyme.

In the absence of target nucleic acid and in the absence of T7 RNA polymerase (FIG. 11b), no fluorescence signal is detected, whether for the probes according to the invention or for the molecular beacon probes. This means that in these experimental conditions, the fluorophore and the quencher are close to one another, permitting "quenching" of the fluorescence. The molecular beacon probes are therefore in a closed conformation, i.e. have a secondary structure of hairpin shape.

The probes according to the invention are in a closed conformation, called circular conformation.

In the presence of T7 RNA polymerase and in the absence of any target nucleic acid, the fluorescence emitted by the probes according to the invention is the same as that measured in the absence of T7 RNA polymerase and in the absence of any target nucleic acid. A "quenching" of fluorescence is also observed here. The probes according to the invention are still in their initial conformation, i.e. in a circular conformation even in the presence of the enzyme.

Conversely, when T7 RNA polymerase enzyme is added to the reaction mixture containing the molecular beacon probes, an increase in the fluorescence signal is observed. This means that the distance between the fluorophore and the quencher has increased. A change in conformation of the molecular beacon occurred during addition of the T7 RNA polymerase. The molecular beacon probes opened. They have a linear conformation as if they had hybridized to their target nucleic acid.

Conclusion:

The results show that the two molecular beacons analyzed, CPinfB and HIV-1A, produce an increase in signal during their incubation in the presence of enzyme T7 RNA Polymerase, whereas the probes according to the invention analyzed in the same conditions do not produce this same increase in signal. This result is verified for all the probes according to the invention tested, whether they have a closing sequence modified at 3' or at 5', and whether they contain alpha or inverted nucleotides. Therefore the probes according to the invention are not sensitive to the effects of contaminants such as T7 RNA polymerase for example. There is no undesirable spontaneous opening of the probes according to the invention, and therefore no emission of a nonspecific signal.

The invention claimed is:

1. A method for detecting a target nucleic acid when present in a sample comprising:
   contacting the sample and a probe, the probe comprising a nucleotide strand that comprises a first fragment having a first closing sequence, a second fragment having a recognition sequence hybridizable to the target nucleic acid under hybridization conditions, a third fragment having a second closing sequence, and at least two markers such that one end of the nucleotide strand of the probe is free of a marker; and
   detecting hybridization of the probe and the target nucleic acid during or after amplification of the target nucleic acid when the target nucleic acid is present in the sample, wherein:
   in the absence of hybridization to the target nucleic acid, the first and second closing sequences are hybridized to each other in parallel under hybridization conditions such that the probe has a completely circular structure, thereby reducing detectability of the probe; and
   the first closing sequence or the second closing sequence comprises alpha nucleotides.

2. The method as claimed in claim 1, wherein a first marker is on a nucleotide of the first fragment and a second marker is on a nucleotide of the second or third fragment, the nucleotide of the first fragment and the nucleotide of the second or third fragment being adjacent when the first and second closing sequences are hybridized.

3. The method as claimed in claim 1, wherein one of the at least two markers is a fluorophore and one of the at least two markers is a fluorescence quencher.

4. The method as claimed in claim 1, wherein all or part of the first closing sequence or all or part of the second closing sequence is hybridizable to the target nucleic acid under hybridization conditions.

5. The method as claimed in claim 1, wherein a nucleotide sequence is attached to an end of one of the first and second closing sequences.

6. The method as claimed in claim 1, wherein detection is performed during amplification of the target nucleic acid.

7. The method as claimed in claim 1, wherein detection is performed after amplification of the target nucleic acid.

8. The method as claimed in claim 1, wherein the probe has greater hybridization specificity under equally stringent hybridization conditions than a stem-loop hairpin molecular beacon having a recognition sequence that is the same as the recognition sequence of the probe.

* * * * *